US010201639B2

(12) United States Patent
Concagh et al.

(10) Patent No.: US 10,201,639 B2
(45) Date of Patent: Feb. 12, 2019

(54) DRUG-ELUTING MEDICAL IMPLANTS

(71) Applicant: 480 Biomedical Inc., Watertown, MA (US)

(72) Inventors: Danny Concagh, Medfield, MA (US); Changcheng You, Northbridge, MA (US)

(73) Assignee: 480 Biomedical, Inc., Watertown, MA (US)

( * ) Notice: Subject to any disclaimer, the term of this patent is extended or adjusted under 35 U.S.C. 154(b) by 0 days.

(21) Appl. No.: 15/583,196

(22) Filed: May 1, 2017

(65) Prior Publication Data

US 2018/0311415 A1 Nov. 1, 2018

(51) Int. Cl.

| | |
|---|---|
| ***A61F 2/06*** | (2013.01) |
| ***A61L 27/28*** | (2006.01) |
| ***A61L 31/10*** | (2006.01) |
| ***A61L 31/02*** | (2006.01) |
| ***A61L 31/14*** | (2006.01) |
| ***A61L 31/16*** | (2006.01) |
| ***A61K 31/337*** | (2006.01) |
| ***A61F 2/88*** | (2006.01) |

(52) U.S. Cl.

CPC ................ *A61L 31/10* (2013.01); *A61F 2/88* (2013.01); *A61K 31/337* (2013.01); *A61L 31/022* (2013.01); *A61L 31/148* (2013.01); *A61L 31/16* (2013.01); *A61F 2210/0004* (2013.01); *A61F 2210/0014* (2013.01); *A61F 2210/0076* (2013.01); *A61F 2230/0091* (2013.01); *A61F 2250/003* (2013.01); *A61F 2250/0067* (2013.01); *A61L 2300/416* (2013.01); *A61L 2400/16* (2013.01); *A61L 2420/06* (2013.01); *A61L 2420/08* (2013.01)

(58) Field of Classification Search

CPC ......... A61F 2/06; A61L 27/227; A61L 131/16

USPC ................................................ 623/1.42–1.48

See application file for complete search history.

(56) References Cited

U.S. PATENT DOCUMENTS

| | | | |
|---|---|---|---|
| 4,886,062 | A | 12/1989 | Wiktor |
| 5,133,732 | A | 7/1992 | Wiktor |
| 5,170,802 | A | 12/1992 | Mehra |
| 5,224,491 | A | 7/1993 | Mehra |
| 5,265,601 | A | 11/1993 | Mehra |
| 5,336,163 | A | 8/1994 | DeMane et al. |
| 5,591,198 | A | 1/1997 | Boyle et al. |
| 5,613,981 | A | 3/1997 | Boyle et al. |
| 5,653,727 | A | 8/1997 | Wiktor |
| 5,897,521 | A | 4/1999 | Lavigne |
| 5,899,934 | A | 5/1999 | Amundson et al. |
| 5,913,896 | A | 6/1999 | Boyle et al. |
| 6,047,431 | A | 4/2000 | Canonica |
| 6,161,029 | A | 12/2000 | Spreigl et al. |
| 6,301,507 | B1 | 10/2001 | Bakels et al. |
| 6,330,481 | B1 | 12/2001 | Van Wijk et al. |
| 6,346,116 | B1 | 2/2002 | Brooks et al. |
| 6,385,491 | B1 | 5/2002 | Lindemans et al. |
| 6,449,507 | B1 | 9/2002 | Hill et al. |
| 6,487,446 | B1 | 11/2002 | Hill et al. |

(Continued)

*Primary Examiner* — Suzette J Gherbi

(74) *Attorney, Agent, or Firm* — Medlen & Carroll, LLP

(57) ABSTRACT

Disclosed are medical implants for placement within a lumen of a patient. The implants comprise a polymer and drug-coated metal structure having a tubular configuration and designed to deliver the drug to target tissue at tailored linear drug elution rate.

10 Claims, 15 Drawing Sheets

(56) References Cited

U.S. PATENT DOCUMENTS

| | | | |
|---|---|---|---|
| 6,532,388 | B1 | 3/2003 | Hill et al. |
| 6,543,452 | B1 | 4/2003 | Lavigne |
| 6,628,987 | B1 | 9/2003 | Hill et al. |
| 6,718,208 | B2 | 4/2004 | Hill et al. |
| 6,770,080 | B2 | 8/2004 | Kaplan et al. |
| 6,863,684 | B2 | 3/2005 | Kim et al. |
| 6,904,318 | B2 | 6/2005 | Hill et al. |
| 6,909,920 | B2 | 6/2005 | Lokhoff et al. |
| 6,923,828 | B1 | 8/2005 | Wiktor |
| 6,945,992 | B2 | 9/2005 | Goodson, IV et al. |
| 7,184,828 | B2 | 2/2007 | Hill et al. |
| 7,184,829 | B2 | 2/2007 | Hill et al. |
| 7,323,008 | B2 | 1/2008 | Kantor et al. |
| 7,356,903 | B2 | 4/2008 | Krivoruchko et al. |
| 7,361,168 | B2 | 4/2008 | Makower et al. |
| 7,386,351 | B2 | 6/2008 | Hine et al. |
| 7,410,480 | B2 | 8/2008 | Muni et al. |
| 7,419,497 | B2 | 9/2008 | Muni et al. |
| 7,462,175 | B2 | 12/2008 | Chang et al. |
| 7,500,971 | B2 | 3/2009 | Chang et al. |
| 7,520,876 | B2 | 4/2009 | Ressemann et al. |
| 7,544,192 | B2 | 6/2009 | Eaton et al. |
| 7,547,323 | B2 | 6/2009 | Lavigne |
| 7,559,925 | B2 | 7/2009 | Goldfarb et al. |
| 7,578,899 | B2 | 8/2009 | Edwin et al. |
| 7,615,072 | B2 | 11/2009 | Rust et al. |
| 7,641,644 | B2 | 1/2010 | Chang et al. |
| 7,645,272 | B2 | 1/2010 | Chang et al. |
| 7,648,367 | B1 | 1/2010 | Makower et al. |
| 7,654,997 | B2 | 2/2010 | Makower et al. |
| 7,662,141 | B2 | 2/2010 | Eaton et al. |
| 7,662,142 | B2 | 2/2010 | Eaton et al. |
| 7,678,099 | B2 | 3/2010 | Ressemann et al. |
| 7,686,798 | B2 | 3/2010 | Eaton et al. |
| 7,691,094 | B2 | 4/2010 | Eaton et al. |
| 7,697,972 | B2 | 4/2010 | Verard et al. |
| 7,704,259 | B2 | 4/2010 | Kaplan et al. |
| 7,713,255 | B2 | 5/2010 | Eaton et al. |
| 7,717,933 | B2 | 5/2010 | Becker |
| 7,717,955 | B2 | 5/2010 | Lane et al. |
| 7,720,521 | B2 | 5/2010 | Chang et al. |
| 7,727,186 | B2 | 6/2010 | Makower et al. |
| 7,727,226 | B2 | 6/2010 | Chang et al. |
| 7,740,642 | B2 | 6/2010 | Becker |
| 7,753,929 | B2 | 7/2010 | Becker |
| 7,753,930 | B2 | 7/2010 | Becker |
| 7,771,409 | B2 | 8/2010 | Chang et al. |
| 7,803,150 | B2 | 9/2010 | Chang et al. |
| 7,806,919 | B2 | 10/2010 | Bloom et al. |
| 7,815,673 | B2 | 10/2010 | Bloom et al. |
| 7,837,727 | B2 * | 11/2010 | Goetz .................. A61F 2/2418 623/1.15 |
| 7,842,062 | B2 | 11/2010 | Keith et al. |
| 7,854,744 | B2 | 12/2010 | Becker |
| 7,951,131 | B2 | 1/2011 | Eaton et al. |
| 7,879,061 | B2 | 2/2011 | Keith et al. |
| 7,914,639 | B2 | 3/2011 | Layne et al. |
| 7,951,130 | B2 | 3/2011 | Eaton et al. |
| 7,918,871 | B2 | 4/2011 | Truitt et al. |
| 7,951,132 | B2 | 5/2011 | Eaton et al. |
| 7,951,133 | B2 | 5/2011 | Eaton et al. |
| 7,951,134 | B2 | 5/2011 | Eaton et al. |
| 7,951,135 | B2 | 5/2011 | Eaton et al. |
| 7,955,346 | B2 | 6/2011 | Mauch et al. |
| 7,967,807 | B2 | 6/2011 | Murray |
| 7,967,857 | B2 | 6/2011 | Lane |
| 7,972,378 | B2 | 7/2011 | Tabor et al. |
| 7,993,350 | B2 | 8/2011 | Ventura et al. |
| 7,993,675 | B2 | 8/2011 | Oliver et al. |
| 8,025,635 | B2 | 9/2011 | Eaton et al. |
| 8,034,099 | B2 | 10/2011 | Pellegrini |
| 8,046,052 | B2 | 10/2011 | Verard et al. |
| 8,048,150 | B2 * | 11/2011 | Weber ...................... A61F 2/07 623/1.15 |
| 8,052,693 | B2 | 11/2011 | Shahoian |
| 8,052,750 | B2 | 11/2011 | Tuval et al. |
| 8,088,101 | B2 | 1/2012 | Chang et al. |
| 8,100,933 | B2 | 1/2012 | Becker |
| 8,109,918 | B2 | 2/2012 | Eaton et al. |
| 8,114,062 | B2 | 2/2012 | Muni et al. |
| 8,114,113 | B2 | 2/2012 | Becker |
| 8,118,757 | B2 | 2/2012 | Morriss |
| 8,123,722 | B2 | 2/2012 | Chang et al. |
| 8,126,549 | B2 | 2/2012 | Sigg et al. |
| 8,142,422 | B2 | 3/2012 | Makower et al. |
| 8,146,400 | B2 | 4/2012 | Goldfarb et al. |
| 8,152,842 | B2 | 4/2012 | Schlun |
| 8,157,940 | B2 | 4/2012 | Edwin et al. |
| 8,172,828 | B2 | 5/2012 | Chang et al. |
| 8,182,432 | B2 | 5/2012 | Kim et al. |
| 8,190,389 | B2 | 5/2012 | Kim et al. |
| 8,192,420 | B2 | 6/2012 | Morriss et al. |
| 8,206,349 | B2 | 6/2012 | Slenker et al. |
| 8,211,169 | B2 | 7/2012 | Lane et al. |
| 8,241,266 | B2 | 8/2012 | Keith et al. |
| 8,249,700 | B2 | 8/2012 | Clifford et al. |
| 8,273,253 | B2 | 9/2012 | Curran |
| 8,277,503 | B2 | 10/2012 | Lavigne |
| 8,277,504 | B2 | 10/2012 | Lavigne |
| 8,282,667 | B2 | 10/2012 | Drontle et al. |
| 8,313,762 | B2 | 11/2012 | Oliver et al. |
| 8,317,816 | B2 | 11/2012 | Becker |
| 8,328,865 | B2 | 12/2012 | Bales, Jr. et al. |
| 8,328,867 | B2 | 12/2012 | Dolan et al. |
| 8,333,799 | B2 | 12/2012 | Bales, Jr. et al. |
| 8,333,800 | B2 | 12/2012 | Bruszewski et al. |
| 8,337,454 | B2 | 12/2012 | Eaton et al. |
| 8,337,650 | B2 | 12/2012 | Edwin et al. |
| 8,348,969 | B2 | 1/2013 | Keith et al. |
| 8,348,995 | B2 | 1/2013 | Tuval et al. |
| 8,348,996 | B2 | 1/2013 | Tuval et al. |
| 8,353,952 | B2 | 1/2013 | Thompson et al. |
| 8,377,083 | B2 | 2/2013 | Mauch et al. |
| 8,414,473 | B2 | 4/2013 | Jenkins et al. |
| 8,414,643 | B2 | 4/2013 | Tuval et al. |
| 8,425,457 | B2 | 4/2013 | John et al. |
| 8,425,488 | B2 | 4/2013 | Clifford et al. |
| 8,435,261 | B2 | 5/2013 | Arcand et al. |
| 8,435,290 | B2 | 5/2013 | Clifford et al. |
| 8,439,687 | B1 | 5/2013 | Morriss et al. |
| 8,452,392 | B2 | 5/2013 | Morriss et al. |
| 8,460,323 | B2 | 6/2013 | Mauch et al. |
| 8,485,199 | B2 | 7/2013 | Morriss |
| 8,500,793 | B2 | 8/2013 | Zipse et al. |
| 8,500,801 | B2 | 8/2013 | Eberhardt et al. |
| 8,529,548 | B2 | 9/2013 | Blott et al. |
| 8,529,941 | B2 | 9/2013 | Hakimimehr et al. |
| 8,535,707 | B2 | 9/2013 | Arensdorf et al. |
| 8,540,694 | B2 | 9/2013 | Flaherty et al. |
| 8,551,156 | B2 | 10/2013 | Wack et al. |
| 8,562,672 | B2 | 10/2013 | Bonhoeffer et al. |
| 8,563,510 | B2 | 10/2013 | Hakimimehr et al. |
| 8,568,439 | B2 | 10/2013 | Keith et al. |
| 8,585,728 | B2 | 11/2013 | Keith et al. |
| 8,585,729 | B2 | 11/2013 | Keith et al. |
| 8,585,730 | B2 | 11/2013 | Eaton et al. |
| 8,585,731 | B2 | 11/2013 | Abbate et al. |
| 8,617,337 | B2 | 12/2013 | Layne et al. |
| 8,623,043 | B1 | 1/2014 | Keith et al. |
| 8,647,379 | B2 | 2/2014 | McDermott et al. |
| 8,647,458 | B2 | 2/2014 | Banas et al. |
| 8,657,846 | B2 | 2/2014 | Keith et al. |
| 8,657,867 | B2 | 2/2014 | Dorn et al. |
| 8,663,192 | B2 | 3/2014 | Hester et al. |
| 8,673,000 | B2 | 3/2014 | Tabor et al. |
| 8,673,099 | B2 | 3/2014 | Bogert |
| 8,691,288 | B2 | 4/2014 | Myntti |
| 8,702,626 | B1 | 4/2014 | Kim et al. |
| 8,702,702 | B1 | 4/2014 | Edwards et al. |
| 8,715,169 | B2 | 5/2014 | Chang et al. |
| 8,721,591 | B2 | 5/2014 | Chang et al. |
| 8,740,839 | B2 | 6/2014 | Eaton et al. |
| 8,740,929 | B2 | 6/2014 | Gopferich et al. |
| 8,747,297 | B2 | 6/2014 | Miyoshi et al. |

(56) References Cited

U.S. PATENT DOCUMENTS 8,747,389 B2 6/2014 Goldfarb et al.
8,747,460 B2 6/2014 Tuval et al.
8,758,420 B2 6/2014 Dorn et al.
8,763,222 B2 7/2014 Abbate et al.
8,764,709 B2 7/2014 Chang et al.
8,764,726 B2 7/2014 Chang et al.
8,764,729 B2 7/2014 Muni et al.
8,764,786 B2 7/2014 Becker
8,765,715 B2 7/2014 Oliver et al.
8,777,017 B2 7/2014 Curran
8,777,911 B2 7/2014 Heagle et al.
8,777,926 B2 7/2014 Chang et al.
8,795,713 B2 8/2014 Makower et al.
8,801,670 B2 8/2014 Drontle et al.
8,801,775 B2 8/2014 Griswold
8,801,776 B2 8/2014 House et al.
8,802,131 B2 8/2014 Arensdorf et al.
8,828,041 B2 9/2014 Chang et al.
8,834,513 B2 9/2014 Hanson et al.
8,834,564 B2 9/2014 Tuval et al.
8,840,602 B2 9/2014 Morris et al.
8,845,619 B2 9/2014 Blott et al.
8,852,143 B2 10/2014 Chang et al.
8,858,586 B2 10/2014 Chang et al.
8,858,974 B2 10/2014 Eaton et al.
8,864,774 B2 10/2014 Liu et al.
8,864,787 B2 10/2014 Muni et al.
8,870,893 B2 10/2014 Makower et al.
8,876,894 B2 11/2014 Tuval et al.
8,876,895 B2 11/2014 Tuval et al.
8,888,686 B2 11/2014 Drontle et al.
8,894,614 B2 11/2014 Muni et al.
8,905,922 B2 12/2014 Makower et al.
8,920,419 B2 12/2014 Edwards et al.
8,926,689 B2 1/2015 Bogert
8,932,276 B1 1/2015 Morriss et al.
8,945,088 B2 2/2015 Chang et al.
8,951,225 B2 2/2015 Evard et al.
8,968,269 B2 3/2015 Becker
8,979,888 B2 3/2015 Morriss et al.
8,986,341 B2 3/2015 Abbate et al.
8,997,998 B2 4/2015 Curran et al.
9,005,284 B2 4/2015 Ressemann
9,011,363 B2 4/2015 Clopp et al.
9,022,967 B2 5/2015 Oliver et al.
9,039,657 B2 5/2015 Makower et al.
9,039,680 B2 5/2015 Makower et al.
9,050,440 B2 6/2015 Becker
9,055,965 B2 6/2015 Chang et al.
9,072,619 B2 7/2015 Lam et al.
9,072,681 B2 7/2015 Hakimimehr et al.
9,078,783 B2 7/2015 Morriss et al.
9,084,691 B2 7/2015 Wack et al.
9,084,876 B2 7/2015 Makower et al.
9,089,258 B2 7/2015 Goldfarb et al.
9,095,364 B2 8/2015 Muni et al.
9,095,646 B2 8/2015 Chow et al.
9,101,384 B2 8/2015 Makower et al.
9,101,739 B2 8/2015 Lesch, Jr. et al.
9,114,040 B2 8/2015 Dorn et al.
9,138,569 B2 9/2015 Edgren et al.
9,144,663 B2 9/2015 Ahlberg et al.
9,192,692 B2 11/2015 Medina et al.
9,192,751 B2 11/2015 Macaulay et al.
9,220,879 B2 12/2015 Chang et al.
9,238,125 B2 1/2016 Vaccaro et al.
9,241,794 B2 * 1/2016 Braido .................. A61F 2/2412
9,241,834 B2 1/2016 Chang et al.
9,271,925 B2 3/2016 Hammerick
9,295,547 B2 3/2016 Costello et al.
9,308,358 B2 4/2016 Oliver et al.
9,308,361 B2 4/2016 Muni et al.
9,320,876 B2 4/2016 Ressemann et al.
9,333,220 B2 5/2016 Tijsma et al.
9,333,365 B2 5/2016 Zhao
9,351,750 B2 5/2016 Muni et al.
9,398,966 B2 7/2016 Thompson
9,402,719 B2 8/2016 Lane
9,427,343 B2 8/2016 Bogert
9,456,897 B2 10/2016 Krivoruchko et al.
9,498,239 B2 11/2016 Schreck et al.
9,504,556 B2 11/2016 Bebb
9,504,812 B2 11/2016 Edgren et al.
9,561,119 B2 2/2017 Eberhardt et al.
9,597,485 B2 3/2017 Edgren et al.
9,622,850 B2 4/2017 Bebb et al.
9,629,644 B2 4/2017 Schreck et al.
9,649,477 B2 5/2017 Muni et al.
9,662,168 B2 5/2017 Edwards et al.
9,675,451 B2 6/2017 Garde et al.
9,681,914 B2 6/2017 Edwards et al.
9,693,859 B2 * 7/2017 Braido .................. A61F 2/2409
9,700,326 B2 7/2017 Morriss et al.
9,707,110 B2 7/2017 McDermott et al.
9,717,612 B2 8/2017 Dorn et al.
2007/0208252 A1 9/2007 Makower
2008/0152784 A1 * 6/2008 Stenzel .................. A61L 31/10 427/2.25
2008/0181927 A1 * 7/2008 Zhao .................. A61K 31/337 424/423
2008/0243140 A1 10/2008 Gopferich et al.
2009/0005863 A1 * 1/2009 Goetz .................. A61F 2/2418 623/2.18
2009/0030499 A1 1/2009 Bebb et al.
2009/0270965 A1 10/2009 Sinha et al.
2009/0287300 A1 * 11/2009 Dave .................. A61L 31/06 623/1.42
2010/0016946 A1 1/2010 McDermott
2010/0131049 A1 5/2010 Perkins et al.
2010/0262224 A1 * 10/2010 Kleiner .................. A61L 31/06 623/1.15
2010/0272778 A1 * 10/2010 McClain .................. A61F 2/82 424/423
2010/0331619 A1 12/2010 Miyoshi et al.
2011/0009951 A1 1/2011 Bogert
2011/0015612 A1 1/2011 Arcand et al.
2011/0054552 A1 3/2011 Takayama et al.
2011/0060214 A1 3/2011 Makower
2011/0118802 A1 5/2011 Usui
2011/0155149 A1 6/2011 Mauch
2011/0257732 A1 * 10/2011 McClain .................. A61F 2/82 623/1.46
2011/0264190 A1 * 10/2011 McClain .................. A61L 31/10 623/1.11
2011/0270379 A1 11/2011 Bruszewski
2012/0035677 A1 2/2012 Imabayashi et al.
2012/0059454 A1 3/2012 Millwee
2012/0071824 A1 3/2012 Chang et al.
2012/0323311 A1 * 12/2012 McClain .................. A61L 31/10 623/1.42
2013/0006055 A1 1/2013 Goldfarb et al.
2013/0035739 A1 2/2013 Goto
2013/0165873 A1 6/2013 Morriss et al.
2013/0231529 A1 9/2013 Chang et al.
2013/0253564 A1 9/2013 Edgren et al.
2013/0261388 A1 10/2013 Jenkins et al.
2013/0282113 A1 10/2013 Punga et al.
2013/0304177 A1 * 11/2013 Palasis .................. A61F 2/90 623/1.2
2013/0304196 A1 11/2013 Kelly
2013/0310780 A1 11/2013 Phillips
2013/0310781 A1 11/2013 Phillips et al.
2013/0317600 A1 * 11/2013 Palasis .................. A61L 31/10 623/1.46
2013/0324970 A1 12/2013 Arcand et al.
2014/0012075 A1 1/2014 Konstorum
2014/0031852 A1 1/2014 Edgren et al.
2014/0031917 A1 1/2014 Thompson
2014/0074140 A1 3/2014 Johnson et al.
2014/0074141 A1 3/2014 Johnson et al.
2014/0079755 A1 3/2014 Eaton et al.
2014/0107763 A1 4/2014 Layne et al.
2014/0107766 A1 4/2014 Banas et al.

(56) References Cited

U.S. PATENT DOCUMENTS

| | | | | |
|---|---|---|---|---|
| 2014/0154236 | A1 | 6/2014 | Hester et al. | |
| 2014/0200444 | A1 | 7/2014 | Kim et al. | |
| 2014/0222144 | A1 | 8/2014 | Eberhardt et al. | |
| 2014/0276408 | A1 | 9/2014 | Abbate | |
| 2014/0276654 | A1 | 9/2014 | Jenkins | |
| 2014/0296898 | A1 | 10/2014 | Chang et al. | |
| 2014/0330372 | A1 | 11/2014 | Weston et al. | |
| 2014/0336693 | A1 | 11/2014 | Goldfarb et al. | |
| 2014/0336694 | A1 | 11/2014 | Becker | |
| 2015/0030654 | A1* | 1/2015 | Roorda | B05D 1/02 424/423 |
| 2015/0119974 | A1 | 4/2015 | Rothstein | |
| 2015/0190555 | A1* | 7/2015 | Mani | A61L 31/16 623/1.13 |
| 2015/0196735 | A1 | 7/2015 | Olig et al. | |
| 2016/0053134 | A1* | 2/2016 | Kumta | A61L 27/04 623/23.72 |
| 2016/0135951 | A1* | 5/2016 | Salahieh | A61F 2/2418 623/2.11 |
| 2017/0072116 | A1* | 3/2017 | Antoni | A61L 27/28 |
| 2017/0112611 | A1* | 4/2017 | Edwin | A61F 2/94 |
| 2017/0319756 | A1* | 11/2017 | Pulapura | A61L 31/042 |
| 2018/0000996 | A1* | 1/2018 | McClain | A61L 31/10 |
| 2018/0021127 | A1* | 1/2018 | Yohanan | A61F 2/2418 623/2.18 |

* cited by examiner

DRUG-ELUTING MEDICAL IMPLANTS

FIELD OF THE INVENTION

The present invention relates to stents, and more specifically, to stents that include a drug and polymer coating on a metallic tubular structure and are intended for placement within a lumen or cavity of a patient.

BACKGROUND

A variety of medical conditions are treatable by the implantation of tubular devices into natural body lumens. For example, it is commonplace to implant metallic stents into the coronary arteries of patients with heart disease following balloon angioplasty to minimize the risk that the arteries will undergo restenosis. Commercial stents have included drug-eluting polymer coatings that are designed to further decrease the risk of restenosis, for example. Other examples of conventional tubular medical implants include woven grafts and stent-grafts that are used to span vascular aneurysms, polymeric tubes and catheters that are used to bypass strictures in the ureter and urethra, and stents that are used in the peripheral vasculature, prostate, and esophagus.

Despite the evolution of metallic stents, they continue to have limitations such as the possibility of causing thrombosis and vascular remodeling. While the use of biodegradable and biostable polymeric materials for stents and other implantable devices has eliminated the possible long-term effects of permanent implants, the use of such materials has been hindered by relatively poor expandability and mechanical properties. For example, the expansion characteristics and radial strength of stents made from biodegradable and biostable polymeric materials has been significantly lower than that of metallic stents. This is particularly the case where such stents are low profile and make use of small diameter fibers or thin walled struts that comprise the stent body. Furthermore, the degradation rate and the manner in which such devices degrade in the body has been difficult to control. Finally, where such devices are used as a drug delivery vehicle, the drug elution rate has been difficult to reproducibly characterize.

Thus, there is, therefore, a need for implantable tubular devices that have strength and other mechanical and drug release properties that are necessary to effectively treat the medical conditions for which they are used.

SUMMARY OF THE INVENTION

The present invention provides implantable coated stents for placement within a lumen or cavity of a patient, which provide a controlled release of therapeutic agent coated thereon to target tissue. The present invention also provides coated implantable stents made by a process that includes the steps of applying a conformal drug-containing coating comprising PLCL, PLA and paclitaxel on the device and applying a second conformal coating of PLCL and PLA at least partially coating the drug-containing coating. In another aspect, the present invention includes a method of treating a patient by delivering the medical device to a target location within the patient. In yet another aspect, the present invention includes a kit that comprises an implantable coated stent of the invention.

The coated stents of the present invention are generally metallic tubular, self-expanding devices. The devices have a combination of structure and composition that provide them with exceptional expandability and mechanical properties when compared with conventional self-expanding devices, as well as exceptional drug elution properties.

In one aspect of the invention, there is provided a coated stent comprising (a) a tubular metallic substrate, (b) a first coating at least partially covering said substrate, said first coating comprising a first biodegradable polymer or blend of biodegradable polymers, and paclitaxel and optionally, (c) a second coating at least partially covering said first coating, said second coating comprising a second biodegradable polymer or blend of biodegradable polymers, wherein said first biodegradable polymer or blend of biodegradable polymers is the same or different from the second biodegradable polymer or blend of biodegradable polymers; and wherein a quantity of paclitaxel released ranges from 0.3 $ng/mm^2$ to 2.5 $ng/mm^2$ of the surface area of the stent per day over a period of time from 5 days to 180 days of submersion in a pH 7.4 phosphate-buffered saline buffer solution containing 2 wt % sodium dodecyl sulfate at 37° C. under action of a rotary shaker, when the buffer solution is removed completely weekly for paclitaxel quantification and replaced with fresh buffer solution. In some embodiments of this aspect, the stent releases paclitaxel in the range of from 0.6 ng to 2.0 $ng/mm^2$ of the surface area of the stent per day. Preferably, the release of paclitaxel during a period of from one to four days of submersion as defined above is 12.5 $ng/mm^2$ of stent surface area per day or less. In a preferred embodiment, the thickness of the first coating is in the range of from 1 to 15 μm and the second coating thickness is in the range of 2 to 35 μm. In a most preferred embodiment of this aspect of the invention, the coated stent comprises (a) a tubular metallic substrate, (b) a first coating at least partially covering said substrate, said coating comprising a blend of poly(L-lactide-co-ε-caprolactone) (PLCL), poly(L-lactide) (PLA), and paclitaxel and (c) a second coating at least partially covering said first coating, said second coating comprising PLCL and PLA.

In another aspect, there is provided a coated stent comprising (a) a tubular metallic substrate, (b) a first coating at least partially covering said substrate, said first coating comprising a first biodegradable polymeric material and paclitaxel and optionally, (c) a second coating comprising a second biodegradable polymeric material at least partially covering the first coating, wherein the first and second biodegradable polymeric material are the same or different; and wherein a quantity of paclitaxel released, based on a total amount of paclitaxel in the coated stent, ranges from 1% to 6% each week from 6 weeks to 20 weeks of submersion in a pH 7.4 phosphate-buffered saline buffer solution containing 2 wt % sodium dodecyl sulfate at 37° C. under action of a rotary shaker, when the buffer solution is removed completely weekly for paclitaxel quantification and replaced with fresh buffer solution. In some embodiments the total amount of paclitaxel contained in the first coating ranges from 2 to 5 wt % of the coating. In certain embodiments, the quantity of paclitaxel released from the stents is in the range of 2 to 4% each week as measured as described above. Preferably, the cumulative release of paclitaxel, based on the total amount of paclitaxel in the stent, is less than 22% over a period of fourteen days of submersion as described above. In certain embodiments, the cumulative release of drug, such as paclitaxel, is less than 10%, preferably less than 7%, and most preferably less than 5% based on total amount of drug in the stent, in the first 24 hours of submersion as described above. In certain embodiments, the total thickness of the first and second coatings is less than 100 μm, less than 50 μm or less than 25 μm.

In another aspect, there is provided a coated stent made by a process comprising:

spray coating a first solution comprising a first solvent or solvent mixture onto a tubular metallic body while rotating the tubular metallic body about a longitudinal axis to form a first wet coating;

heating said tubular body after said step of spray coating said first solution onto said tubular body at a temperature and time duration to cause substantially all of said first solvent or solvent mixture to evaporate from said first wet coating, forming a first dry coating;

optionally spray coating a second solution comprising a second solvent or solvent mixture onto said tubular body after forming said first dry coating to form a second wet coating, the second wet coating conformally coating at least a portion of the first dry coating; and heating said tubular body after said step of spray coating said second solution onto said tubular body at a temperature and time duration to cause substantially all of said second solvent or solvent mixture to evaporate from said second wet coating, forming a second dry coating;

wherein said first and second dry coatings have a combined thickness of less than 50 microns;

wherein the first solution comprises a first set of solids in the first solvent or solvent mixture, said first set of solids comprising 10 to 99 weight percent of poly(L-lactide-co-ε-caprolactone) (PLCL), 1 to 90 weight percent of poly(L-lactide) (PLA), and 0.1-20 weight percent of paclitaxel, wherein the weight percentage of the first set of solids in the first solvent or solvent mixture is in the range of from 1 to 5 weight percent;

wherein the second solution comprises a second set of solids in the second solvent or solvent mixture, said second set of solids comprising 10 to 99 weight percent of PLCL and 1 to 90 weight percent of PLA, wherein the weight percentage of the second set of solids in the second solvent or solvent mixture is in the range of from 0.5 to 2 weight percent; and wherein a quantity of paclitaxel released ranges from 0.3 $ng/mm^2$ to 2.5 $ng/mm^2$ of the surface area of the stent per day over a period of from 5 days to 180 days of submersion in a pH 7.4 phosphate-buffered saline buffer solution containing 2 wt % sodium dodecyl sulfate at 37° C. under action of a rotary shaker, when the buffer solution is removed completely weekly for paclitaxel quantification and replaced with fresh buffer solution. In certain embodiments of this aspect of the invention, the PLCL has a molar percentage of lactide ranging from 60% to 80% and a molar percentage of caprolactone ranging from 20% to 40%. In another embodiment, the PLCL has a molar percentage of lactide ranging from 65% to 75% and a molar percentage of caprolactone ranging from 25% to 35%; and in another embodiment, the PLCL has a molar percentage of lactide ranging from 68% to 72% and a molar percentage of caprolactone ranging from 28% to 32%. Alternatively, the weight ratio of PLCL to PLA in each of the first coating and the second coating ranges from 15:85 to 35:65, or from 20:80 to 30:70. Preferably, the amount of paclitaxel in the first coating ranges from 2 to 5 wt %, such as 3 to 4 wt %. In an embodiment, the combined thickness of the two coatings is less than 100 microns, preferably less than 50 microns, and more preferably less than 25 microns.

In another aspect, the present invention provides a method of treating a subject comprising delivering a stent of the invention to a target site within a body lumen of a subject in need of treatment, wherein a therapeutic amount of paclitaxel is released at the target site, based on a total amount of paclitaxel in the coated stent, ranging from 0.03 $ng/mm^2$ to 2.5 $ng/mm^2$ of the surface area of the stent per day for a period of time of from 5 days to 180 days of submersion in a pH 7.4 phosphate-buffered saline buffer solution containing 2 wt % sodium dodecyl sulfate at 37° C. under action of a rotary shaker, when the buffer solution is removed completely weekly for paclitaxel quantification and replaced with fresh buffer solution.

BRIEF DESCRIPTION OF THE DRAWINGS

FIG. 7A is a graph showing the cumulative percent mass of PTx released from drug coated EverFlex® Exp098A&B as a function of time. FIG. 7B is a graph showing the amount in μg/day of PTx release from drug coated EverFlex® Exp098A&B.

DETAILED DESCRIPTION OF THE INVENTION

Figure 2:
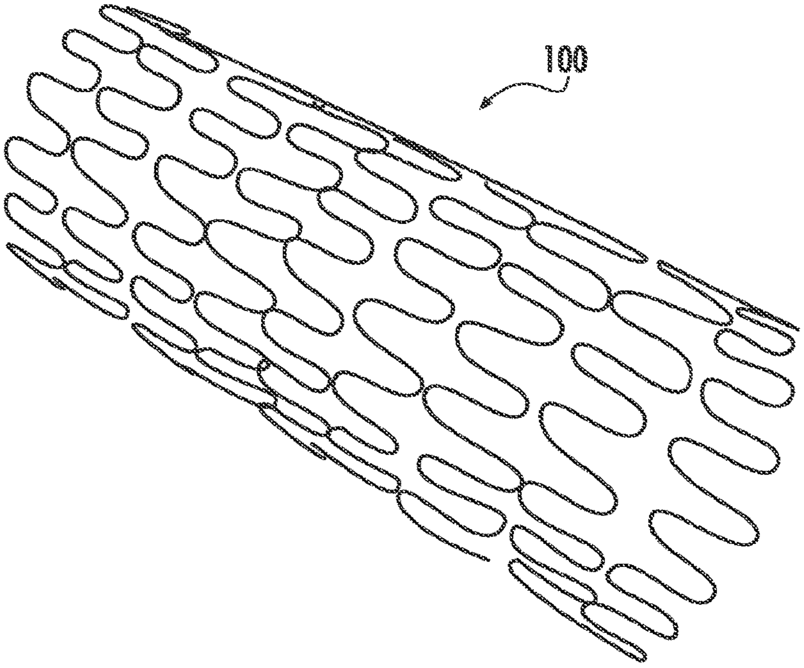
FIG. 2 is a side view of an implantable non-woven medical device, in accordance with an embodiment of the present invention.

As used herein, "stent" is used synonymously with scaffolds, endoprostheses or other substantially tubular structures that may be implanted into the human body. Further, although the present invention may be described with specific reference to stents, it may be applied to any suitable implantable materials and structures. The stents of the present invention comprise a woven or non-woven structure. In one embodiment the stents are described to comprise "strands," which, as used herein, include fibers, extruded elements, struts and other flexible and inflexible elements formed by any suitable method that are movable with respect to each other. The one or more strands of the implants of the present invention are said to be in "proximity" to each other, meaning that they are in physical contact or sufficiently close to being in physical contact and may overlap one another without being affixed to one another. In another embodiment of the invention, the implant is a non-woven, self-expanding structure, such as a unitary framework. As shown in FIG. 2, the non-woven implant 100 is preferably characterized by a regular, repeating pattern such as a lattice structure. When the implant 100 is a unitary framework, it is fabricated using any suitable technique, such as by laser cutting a pattern into a solid polymer tube. In a preferred embodiment, when the implant 100 is a unitary framework, it is formed by laser cutting. It should be recognized that while the present invention is described primarily with reference to non-woven strand configurations, aspects of the present invention are equally applicable to woven, self-expanding structures unless necessarily or expressly limited to non-woven configurations.

Also as used herein, "self-expanding" is intended to include devices that are crimped to a reduced configuration for delivery into a bodily lumen or cavity, and thereafter tend to expand to a larger suitable configuration, such as their original configuration ("as-manufactured" configuration), once released from the delivery configuration. As used herein, "strength" and "stiffness" are used synonymously to mean the resistance of the implants of the present invention to deformation by radial forces. The term "bioabsorbable" is used herein synonymously with "biodegradable" and "bioerodible" to describe a material or structure that degrades in the human body by any suitable mechanism. As used herein, "woven" is used synonymously with "braided."

Figure 1:
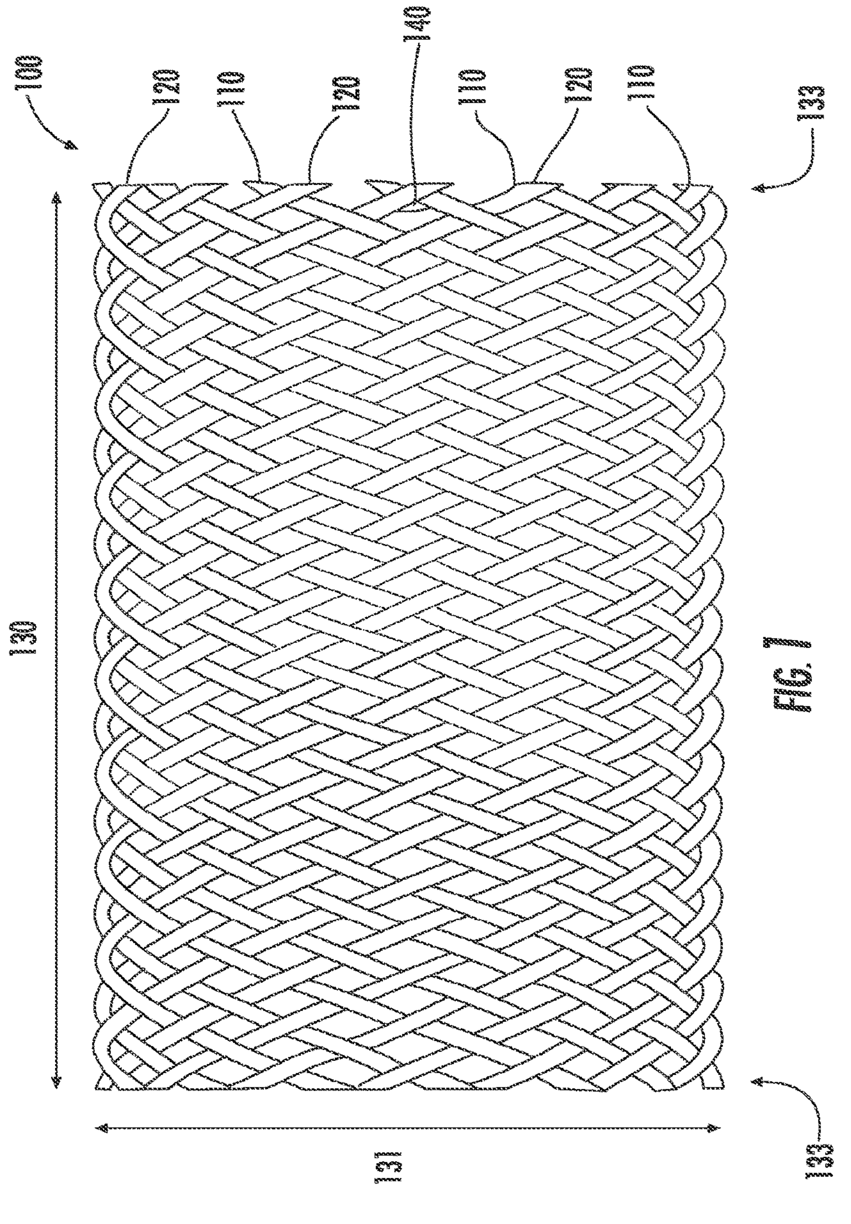
FIG. 1 is a side view of an implantable braided medical device, in accordance with an embodiment of the present invention.

In one embodiment shown in FIG. 1, the implant 100 preferably comprises at least one metallic strand woven together to form a substantially tubular configuration having a longitudinal dimension 130, a radial dimension 131, and first and second ends 132, 133 along the longitudinal dimension. As used herein, "strand," "fiber," and "strut" are used synonymously to mean the elements that define the implant configuration. The tubular configuration of the implant may be woven from a single strand or two or more sets of strands, such as strands 110 and 120, may be woven to form a tubular structure with each set extending in opposed helix configuration along the longitudinal dimension of the implant. In some embodiments, the single strand or sets of strands are woven so as to cross each other at a braid angle 140, which may be constant or may change along the longitudinal dimension of the implant. Preferably, there are between about 2 and 20 strands, more preferably between 5 and 12 strands used in the implants of the present invention, and the braid angle 140 is within the range of about 90 degrees to about 150 degrees throughout the implant. The strands are woven together using methods known in the art, using known weave patterns such as Regular pattern "1 wire, 2-over/2-under", Diamond half load pattern "1 wire, 1-over/1-under", or Diamond pattern "2 wire, 1-over/1-under." Preferably, the strands are not joined or fixed at the plurality of crossover points where the strands intersect or overlap.

The one or more strands can be made of any conventional biocompatible metal materials used for medical implants. Strands may be made from biodegradable metallic materials such as magnesium or zinc, or from biostable metallic materials such as stainless steel, chromium-cobalt alloys, platinum-chromium alloys, nitinol or other suitable biocompatible materials.

In a preferred embodiment, the coated tubular body of the implant is a woven self-expanding stent constructed from nitinol or other biocompatible metal comprising from two to six pairs of closed-ended interwoven wires arranged in a helical pattern designed to be both flexible and resistant to stress fracture. The strands are not affixed to one another at the points of overlap. Alternatively, the self-expanding stent is a non-woven structure preferably constructed from nitinol or other biocompatible metal.

The strands used in the implant 100 preferably have a cross-sectional diameter in the range of from about 0.003 inches to about 0.009 inches, with embodiments including 0.003, 0.004, 0.005, 0.006, 0.007, 0.008 and 0.009 inches, and intervals there between. Where multiple strands are used, they may be of substantially equal diameters within this range, or each strand set may be of a different general diameter than other strand sets comprising the implant. In some embodiments, multiple strand sets are used with different diameters such that the implant includes two, three, four or more different diameter strands. In general, the diameters of strands are chosen so as to render the implant 100 preferably deliverable from a 10 French delivery catheter (i.e., 3.3 mm diameter) or smaller, and more preferably from a 7 French delivery catheter (i.e., 2.3 mm diameter) or 6 French delivery catheter. The ability to place the implant of the present invention into small diameter delivery catheters allows for its implantation into small diameter bodily lumens and cavities, such as those found in the vascular, biliary, uro-genital, iliac, and tracheal-bronchial anatomy. Exemplary vascular applications include coronary as well as peripheral vascular placement, such as in the superficial femoral artery (SFA). It should be appreciated, however, that the implants of the present invention are equally applicable to implantation into larger bodily lumens, such as those found in the gastrointestinal tract, for applications such as esophageal scaffolds.

To provide a desired drug elution profile, the polymer content of each of the coatings may be the same or different. The innermost polymer coating, i.e., the coating applied directly to the stent tubular body, includes a therapeutic agent that provides a desired biological effect upon implantation of the medical device (referred to herein as the "Drug Coat," "DC" or "first coating"). The therapeutic agent(s) used in the present invention are any suitable agents having desired biological effects. In a preferred embodiment, the therapeutic agent used in the present invention is paclitaxel, its analogs, or derivatives. In preferred embodiments, paclitaxel is the sole therapeutic agent contained in the stent.

An optional, second biodegradable polymer coating may be applied over the Drug Coat to form a conformal outer coating (referred to herein as the "Top Coat," "TC" or "second coating") at least partially coating the Drug Coat. The Top Coat may also contain a therapeutic agent, which may be the same or different from the therapeutic agent contained in the Drug Coat, e.g., paclitaxel. In preferred embodiments, the Top Coat is applied to at least a portion of the Drug Coat and does not contain a therapeutic agent.

The Drug Coat and Top Coat (when present) conformally coat at least a portion of the surface of the implant 100. A "conformal" coating as used herein is a coating that generally conforms to the shape of the underlying tubular body. The biodegradable polymers of the Drug Coat and Top Coat provide a desired elution profile for the therapeutic agent contained within the Drug Coat and optionally, the Top Coat, e.g., a substantially linear drug release as described herein below for up to two months, three months, four months, five months, six months or longer, following a short (e.g., less than 14 days, or four days or less, or one day or less) initial burst of drug release, as measured by submerging the coated stent over a period of time from 5 days to 180 days in a pH 7.4 phosphate-buffered saline buffer solution containing 2 wt % sodium dodecyl sulfate at 37° C. under action of a rotary shaker, wherein the buffer solution is removed completely weekly for drug quantification and replaced with fresh buffer solution.

Preferably, the molecular weight of the polymers included in the Drug Coat and Top Coat are between about 5,000 and 350,000 g/mol, preferably between 10,000 and 300,000 g/mol. Polymers according to the present invention are any that facilitate attachment of the therapeutic agent, such as paclitaxel to the stent and/or facilitate the controlled release of therapeutic agent. Preferably, the polymers are used to regulate the release of therapeutic agent to obtain a substantially linear release of the therapeutic agent over time, following an initial short release burst of therapeutic agent, as discussed in detail below. The skilled person will understand that the type of polymer or combination of polymers, concentration of polymers, and thickness of the Drug Coat and Top Coat, can be adjusted to obtain the desired drug release profile.

Polymers suitable for use in the present invention are any biodegradable polymers that are capable of attaching to the stent and releasing paclitaxel or other therapeutic agent. The polymers are biocompatible to minimize irritation of the vessel wall and are biodegradable. Suitable polymers that may be used in the Drug Coat, Top Coat or both include aliphatic polyesters, poly(amino acids), copoly(ether-esters), polyalkylenes oxalates, polyamides, poly(iminocarbonates), polyanhydrides, polyorthoesters, polyoxyesters, polyamidoesters, polylactic acid (PLA), polyethylene oxide (PEO), polycaprolactone (PCL), poly(trimethylene carbonate), poly(fumaric acid), polyaspirin, polyhydroxybutyrate valerates, polyoxaesters containing amido groups, polyphosphazenes, poly (ester amides) silicones, hydrogels, biomolecules and blends thereof.

Aliphatic polyesters include homopolymers and copolymers of lactide (which includes lactic acid D-, L- and meso lactide), ε-caprolactone, glycolide (including glycolic acid), hydroxybutyrate, hydroxyvalerate, para-dioxanone, trimethylene carbonate (and its alkyl derivatives), 1,4-dioxepan-2-one, 1,5-dioxepan-2-one, 6,6-dimethyl-1,4-dioxan-2-one and polymer blends thereof.

Other biodegradable polymers for the purpose of this invention include naturally occurring materials that are enzymatically degraded in the human body or are hydrolytically unstable in the human body such as fibrin, fibrinogen, collagen, gelatin, glycosaminoglycans, elastin, and absorbable biocompatible polysaccharides such as chitosan, starch, fatty acids (and esters thereof), glucoso-glycans and hyaluronic acid.

Other polymers suitable for use in the present invention are biodegradable elastomers, such as aliphatic polyester elastomers. Preferably the bioabsorbable elastomers are based on aliphatic polyesters, including but not limited to elastomeric copolymers of ε-caprolactone and glycolide (preferably having a mole ratio of ε-caprolactone to glycolide of from 80:20 to 60:40, more preferably from 75:25 to 65:35 and most preferably 72:28 to 68:32), elastomeric copolymers of lactide, including L-lactide, D-lactide blends thereof and ε-caprolactone (PLCL) (preferably having a mole ratio of lactide to ε-caprolactone of 80:20 to 60:40, from 75:25 to 65:35, or from 72:28 to 68:32), elastomeric copolymers of p-dioxanone (1,4-dioxan-2-one) and lactide including L-lactide, D-lactide and lactic acid (preferably having a mole ratio of p-dioxanone to lactide of from 30:70 to 70:30, 45:55 to about 55:45, and preferably from 40:60 to 60:40), elastomeric copolymers of ε-caprolactone and p-dioxanone (preferably having a mole ratio of ε-caprolactone to p-dioxanone of from 40:60 to 60:40 and preferably from 30:70 to 70:30) elastomeric copolymers of p-dioxanone and trimethylene carbonate (preferably having a mole ratio of p-dioxanone to trimethylene carbonate of from 40:60 to 60:40, and preferably from 30:70 to 70:30), elastomeric copolymers of trimethylene carbonate and glycolide (preferably having a mole ratio of trimethylene carbonate to glycolide of from 40:60 to 60:40 and preferably from 30:70 to 70:30), elastomeric copolymer of trimethylene carbonate and lactide including L-lactide, D-lactide, blends thereof or lactic acid copolymers (preferably having a mole ratio of trimethylene carbonate to lactide of from 30:70 to 70:30) and blends thereof. As is well known in the art these aliphatic polyester copolymers have different hydrolysis rates, and therefore, the choice of elastomer for the Drug Coat and/or Top Coat may in part be based on the requirements for the coatings adsorption, patency and drug release. Mixtures of fast hydrolyzing and slow hydrolyzing polymers can be used to adjust the time of strength retention and drug release.

In certain embodiments, the Drug Coat and Top Coat each comprise a blend of PLCL and PLA. For example, the polymers of each of the Drug Coat and Top Coat may be blend of PLCL and PLA at a weight ratio of from 15:85 to 35:65 (PLCL:PLA), more preferably from 20:80 to 30:70. Alternatively, the polymers of the each of the Drug Coat and Top Coat may be a blend of PLCL and PLA at a weight ratio of from 40:60 to 60:40, and more preferably 45:55 to 55:45. In other embodiments, the polymer composition of the Drug Coat and Top Coat is PLCL (70:30) and PLA, wherein the weight ratio of PLCL to PLA is 50:50. In other embodiments, the polymer composition of the Drug Coat and Top Coat is PLCL (70:30) and PLA, wherein the weight ratio of PLCL to PLA is 25:75.

In addition to the biodegradable polymers, the Drug Coat also contains therapeutic agent(s), preferably paclitaxel, and more preferably, paclitaxel as the sole therapeutic agent in the stent. For example, the Drug Coat may contain from 0.05 to 20 weight percent, more preferably from 0.1 to 20 weight percent, from 0.5 to 1.25 wt %, from 0.75 to 1 weight percent, from 1.25 to 3.75 weight percent, from 3 to 4 weight percent or from 2 to 5 weight percent paclitaxel. In some embodiments, the Top Coat also contains paclitaxel or other therapeutic agent, at the same or different weight percent as the Drug Coat. Preferably, the Top Coat does not contain therapeutic agent.

In preferred embodiments, the total amount of paclitaxel contained within the stent is in the range of from 0.02 to 0.400 $\mu g/mm^2$ of the surface area of the stent. The total amount of paclitaxel in the stent, when expressed in term of the length of the device is preferably in the range of from 10 μg/10 mm length to 80 μg/10 mm length of the device and more preferably from 10 μg to 50 μg per 10 mm length of stent.

In certain embodiments, the Drug Coat comprises from 10 to 99 weight % of PLCL, 1 to 90 weight % of PLA and 0.1 to 20 weight % of paclitaxel. In other embodiments, the Top Coat comprises 10 to 90 weight % of PLCL and 10 to 90 weight % of PLA. In a preferred embodiment, the Drug Coat comprises from 10 to 99 weight % of PLCL, 1 to 90 weight % of PLA and 2 to 5 weight % of paclitaxel as the sole therapeutic agent and the Top Coat comprises 10 to 90 weight % of PLCL and 10 to 90 weight % of PLA and lacks therapeutic agent.

The amount of each of the coatings applied to the implant 100 has been identified as one of the factors that contribute to the elution rate of therapeutic agent from the implant. The thickness of the coatings has also been found to influence the structural integrity of the coatings upon lengthening and shortening of the implant during and following deployment of the device, particularly at the points of overlap of strand(s). Preferably, the coatings are applied to the implant of the invention to provide a total thickness of less than about 100 microns, preferably less than 50 microns and more preferably, less than about 25 microns.

In certain embodiments, the thickness of the Drug Coat is in the range of from 1 to 25 microns, preferably from 1 to 15 microns, and more preferably from 3 to 5 microns. Preferably, the thickness of the Top Coat is in the range of from 1 to 35 microns, such as from 5 to 12 microns or from 4 to 8 microns or 5 to 10 microns. In some embodiments, the Drug Coat has a thickness of from 10 to 20 microns and the Top Coat has a thickness of from 4 to 8 microns. In other embodiments, the Drug Coat has a thickness of from 3 to 5 microns and the Top Coat has a thickness of from 5.5 to 8.5 microns. In yet other embodiments, the Drug Coat has a thickness of from 1 to 15 microns and the Top Coat has a thickness of 1 to 35 microns and in other embodiments, the Drug Coat has a thickness of 3 to 5 microns and the Top Coat has a thickness of 5 to 10 microns. The ratio of the thickness of the Drug Coat to the thickness of the Top Coat can be varied and may be, for example, in the range of from 0.5 to 2.5, from 1 to 4, from 2 to 3, from 1.25 to 2.5, from 1.25 to 3.75, or from 1.5 to 2.0.

In certain preferred embodiments, the coated metal stent comprises a weight ratio of PLCL to PLA in each of the Drug Coat and Top Coat in the range of from 15:85 and 35:65, more preferably from 20:80 to 30:70, and the Drug Coat contains from 2 to 5 weight %, more preferably from 3 to 4 weight % paclitaxel. The ratio of the thickness of the Drug Coat to the Top Coat in such preferred embodiments is preferably from 0.5 to 2.5, and more preferably from 0.5 to 1.5. Preferably, the Drug Coat thickness is from 1 to 10 microns, such as 3 to 5 microns, and the Top Coat thickness is from 4 to 20 microns, such as 5.5-8.5 microns.

Each of the coated metallic stents of the invention releases therapeutic agent(s) contained therein in a substantially linear manner for up to two, three, four, five or more months following a short, e.g., seven days or less, initial burst of drug release. The therapeutic agent(s) used in the present invention are any suitable agents having desired biological effects, such as an anti-proliferative effect. For example, where the implant of the present invention is used to combat restenosis, the therapeutic agent is selected from anti-thrombogenic agents such as heparin, heparin derivatives, urokinase, and PPack (dextrophenylalanine proline arginine chloromethylketone), enoxaparin, hirudin; anti-proliferative agents such as angiopeptin, or monoclonal antibodies capable of blocking smooth muscle cell proliferation, acetylsalicylic acid, paclitaxel, sirolimus, tacrolimus, everolimus, zotarolimus, vincristine, sprycel, amlodipine and doxazosin; anti-inflammatory agents such as glucocorticoids, betamethasone, dexamethasone, prednisolone, corticosterone, budesonide, estrogen, sulfasalazine, rosiglitazone, mycophenolic acid, and mesalamine; immunosuppressants such as sirolimus, tacrolimus, everolimus, zotarolimus, and dexamethasone; antineoplastic/antiproliferative/anti-mitotic agents such as paclitaxel, 5-fluorouracil, cisplatin, vinblastine, cladribine, vincristine, epothilones, methotrexate, azathioprine, halofuginone, adriamycin, actinomycin and mutamycin; endostatin, angiostatin and thymidine kinase inhibitors, and its analogs or derivatives; anesthetic agents such as lidocaine, bupivacaine, and ropivacaine; anti-coagulants such as D-Phe-Pro-Arg chloromethyl ketone, an RGD peptide-containing compound, heparin, antithrombin compounds, platelet receptor antagonists, anti-thrombin antibodies, anti-platelet receptor antibodies, aspirin (aspirin is also classified as an analgesic, antipyretic and anti-inflammatory drug), dipyridamole, hirudin, prostaglandin inhibitors, platelet inhibitors and antiplatelet agents such as trapidil or liprostin, tick antiplatelet peptides; DNA demethylating drugs such as 5-azacytidine, which is also categorized as a RNA or DNA metabolite that inhibit cell growth and induce apoptosis in certain cancer cells; vascular cell growth promotors such as growth factors, Vascular Endothelial Growth Factors (VEGF, all types including VEGF-2), growth factor receptors, transcriptional activators, and translational promotors; vascular cell growth inhibitors such as antiproliferative agents, growth factor inhibitors, growth factor receptor antagonists, transcriptional repressors, translational repressors, replication inhibitors, inhibitory antibodies, antibodies directed against growth factors, bifunctional molecules consisting of a growth factor and a cytotoxin, bifunctional molecules consisting of an antibody and a cytotoxin; cholesterol-lowering agents; vasodilating agents; and agents which interfere with endogenous vasoactive mechanisms; anti-oxidants, such as probucol; antibiotic agents, such as penicillin, cefoxitin, oxacillin, tobranycin; angiogenic substances, such as acidic and basic fibrobrast growth factors, estrogen including estradiol (E2), estriol (E3) and 17-Beta Estradiol; drugs for heart failure, such as digoxin, beta-blockers, angiotensin-converting enzyme (ACE) inhibitors including captopril and enalopril, statins and related compounds; and macrolides such as sirolimus and everolimus. Preferred therapeutic agents used in the present invention to treat restenosis and similar medical conditions include sirolimus, everolimus, zotarolimus, vincristine, sprycel, dexamethasone, paclitaxel, and analogs thereof. Also preferred is the use of agents that have a primary mechanism of action of inhibiting extracellular matrix remodeling, and a secondary mechanism of action of inhibiting cell proliferation. Such agents include 5-fluorouracil, valsartan, doxycyclin, carvedilol, curcumin, and tranilast.

Elution of therapeutic agent from the inventive stents is described herein in terms of paclitaxel release, but is applicable to any therapeutic agent or combination of therapeutic agents included in the Drug Coat and optionally, the Top Coat. In general, a cumulative release of paclitaxel, based on a total amount of paclitaxel (or other therapeutic agent) in the Drug Coat is no greater than 22% during a period of from 1 to 14 days of submersion in a pH 7.4 phosphate-buffered saline buffer solution containing 2 wt % sodium dodecyl sulfate at 37° C. under action of a rotary shaker, when the buffer solution is removed substantially completely on a weekly basis for paclitaxel quantification (or any therapeutic agent contained in the stent) and replaced with fresh buffer solution. In particular, the cumulative release of drug, such as paclitaxel, is less than 10%, more preferably less than 7%, and most preferably less than 5% based on total amount of drug in the stent, in the first 24 hours of submersion as described above.

Further, the quantity of paclitaxel released from the coated stents described herein, based on a total amount of paclitaxel in the coated stent, ranges from 1% to 8%, preferably from 1% to 6% and more preferably from 2% to 4% each week from six weeks to twenty weeks of submersion in a pH 7.4 phosphate-buffered saline buffer solution containing 2 wt % sodium dodecyl sulfate at 37° C. under action of a rotary shaker, when the buffer solution is removed substantially completely on a weekly basis for quantification and replaced with fresh buffer solution. In certain embodiments, the cumulative release of paclitaxel, based on the total amount of paclitaxel contained in the coated stents of the invention, (a) ranges from 25% to 45% after 6 weeks of submersion in a pH 7.4 phosphate-buffered saline buffer solution containing 2 wt % sodium dodecyl sulfate at 37° C. under action of a rotary shaker, when the buffer solution is removed substantially completely on a weekly basis for paclitaxel quantification and replaced with fresh buffer solution, (b) ranges from 32% to 52% after 8 weeks of said submersion, (c) ranges from 38% to 58% after 10 weeks of said submersion, (d) ranges from 43% to 63% after 12 weeks of said submersion, (e) ranges from 49% to 69% after 14 weeks of said submersion, (f) ranges from 54% to 74% after 16 weeks of said submersion, (g) ranges from 60% to 80% after 18 weeks of said submersion, and (h) ranges from 68% to 88% after 20 weeks of said submersion.

In certain embodiments, the inventive stent is a metallic tubular substrate, such as a braided metallic stent, having a Drug Coat that conformally coats at least a portion of the metallic tubular substrate and which comprises a blend of PLCL, PLA and paclitaxel; a Top Coat comprising PLCL and PLA which at least partially coats the Drug Coat; and which has an elution profile of paclitaxel, based on the total amount of paclitaxel in the coated stent, that ranges from (a) 25% to 45% after 6 weeks of submersion in a pH 7.4 phosphate-buffered saline buffer solution containing 2 wt % sodium dodecyl sulfate at 37° C. under action of a rotary shaker, when the buffer solution is removed substantially completely on a weekly basis for quantification and replaced with fresh buffer solution, (b) ranges from 32% to 52% after 8 weeks of said submersion, (c) ranges from 38% to 58% after 10 weeks of said submersion, (d) ranges from 43% to 63% after 12 weeks of said submersion, (e) ranges from 49% to 69% after 14 weeks of said submersion, (f) ranges from 54% to 74% after 16 weeks of said submersion, (g) ranges from 60% to 80% after 18 weeks of said submersion, and (h) ranges from 68% to 88% after 20 weeks of said submersion.

The quantity of paclitaxel released from the coated stents described herein preferably ranges from 0.3 $ng/mm^2$ to 2.5 $ng/mm^2$ of the surface area of the stent per day or from 0.6 $ng/mm^2$ to 2.0 $ng/mm^2$ of the surface area of the stent per day, and more preferably from 0.375 $ng/mm^2$ to 2.5 $ng/mm^2$ of the surface area of the stent per day as measured over a period of time of from 5 days to 180 days of submersion in a pH 7.4 phosphate-buffered saline buffer solution containing 2 wt % sodium dodecyl sulfate at 37° C. under action of a rotary shaker, when the buffer solution is removed substantially completely on a weekly basis for paclitaxel quantification and replaced with fresh buffer solution. In certain embodiments, the quantity of paclitaxel released from the inventive stents during a period of from one to four days of submersion in a pH 7.4 phosphate-buffered saline buffer solution containing 2 wt % sodium dodecyl sulfate at 37° C. under action of a rotary shaker, when the buffer solution is removed completely weekly for quantification and replaced with fresh buffer solution is generally 12.5 $ng/mm^2$ of stent surface area per day or less.

In certain preferred embodiments, the coated metal stent comprises an innermost Drug Coat containing an amount of paclitaxel and a blend of PLCL and PLA coating at least a portion of the metal stent and a Top Coat containing a blend of PLCL and PLA, at least partially coating the Drug Coat. The thus coated stent releases an amount of paclitaxel from the Drug Coat in the range of from 0.3 ng/mm2 to 2.5 ng/mm2 of the stent surface per day over a period of from 5 days to 180 days of submersion in a pH 7.4 phosphate-buffered saline buffer solution containing 2 wt % sodium dodecyl sulfate at 37° C. under action of a rotary shaker, when the buffer solution is removed substantially completely on a weekly basis for quantification and replaced with fresh buffer solution. Such preferred stents have a paclitaxel-containing Drug Coat and a Top Coat that contains no therapeutic agent. Preferably, paclitaxel is the sole therapeutic agent contained in the stent. Such stents may comprise one or more metallic strands, such as opposing sets of helical metallic strands, which form a plurality of intersections at portions of the strands that slidably overlap one another. In a preferred embodiment the metal strands comprise nitinol.

The ratio of the thickness of the Drug Coat to the thickness of the Top Coat for such stents of is preferably in the range of from 0.5 to 2.5 or from 0.5 to 1.0. In preferred embodiments, the Drug Coat thickness ranges from 1 to 15 μm and the Top Coat ranges from 2 to 35 μm.

Preferably, the PLCL of these preferred embodiments has a molar percentage of lactide ranging from 60 to 80% and a molar percentage of caprolactone ranging from 20% to 40%; in other embodiments the PLCL has a molar percentage of lactide ranging from 65 to 75% and a molar percentage of caprolactone ranging from 25% to 35%; and in other embodiments the PLCL has a molar percentage of lactide ranging from 68 to 72% % and a molar percentage of caprolactone ranging from 28% to 32%. Preferably, the weight ratio of PLCL to PLA in each of the Drug Coat and Top Coat ranges from 15:85 to 35:65, from 20:80 to 30:70, from 45:55 to 55:45 or, most preferably, from 40:60 to 60:40.

In a most preferred embodiment, the weight ratio of PLCL to PLA in each of the Drug Coat and Top Coat is in the range of from 40:60 to 60:40 and the Drug Coat contains from 0.5 to 1.25, more preferably from 0.75 to 1 weight % paclitaxel. The ratio of the thickness of the Drug Coat to the Top Coat in such most preferred embodiments ranges from 1.25 to 3.75, and more preferably from 2 to 3 and preferably, the Drug Coat thickness is from 10 to 20 microns and the Top Coat thickness is from 4 to 8 microns.

In these preferred embodiments, the total amount of paclitaxel in such stents is in the range of from 10 μg to 80 μg per 10 mm length of stent, more preferably 10 to 50 μm per 10 mm length of stent, or in the range of from 0.02 to 0.400 $\mu g/mm^2$ of the surface area of the stent. Preferably, the total amount of paclitaxel in the Drug Coat ranges from 2 to 5 wt %, or from 3 to 4 wt % of the coating. The total amount of paclitaxel released from such stents, based on the total amount of paclitaxel in the stent, is preferably in the range of from 2% to 4% each week from 6 weeks to 20 weeks as measured by a submersion assay as described above. In some embodiments, the total amount of paclitaxel released from such coated stents, based on the total amount of paclitaxel in the stent, (a) ranges from 25% to 45% after 6 weeks of submersion in a pH 7.4 phosphate-buffered saline buffer solution containing 2 wt % sodium dodecyl sulfate at 37° C. under action of a rotary shaker, when the buffer solution is removed substantially completely on a weekly basis for paclitaxel quantification and replaced with fresh buffer solution, (b) ranges from 32% to 52% after 8 weeks of such submersion, (c) ranges from 38% to 58% after 10 weeks of such submersion, (d) ranges from 43% to 63% after 12 weeks of such submersion, (e) ranges from 49% to 69% after 14 weeks of such submersion, (f) ranges from 54% to 74% after 16 weeks of such submersion, (g) ranges from 60% to 80% after 18 weeks of such submersion, and (h) ranges from 68% to 88% after 20 weeks of such submersion.

In another aspect of the invention, coated metallic stents as described herein are made by a process that includes separately forming one or more polymeric coating solutions and applying the coating solution(s) to the tubular device in a step-wise manner. A first biodegradable polymeric coating solution that includes at least one therapeutic agent, such as paclitaxel, is formed and optionally, a biodegradable second polymeric coating solution is formed. The first polymeric coating solution containing therapeutic agent is applied directly to the metallic stent body to thereby form a Drug Coat directly on and at least partially coating the stent and optionally, a second polymeric solution is applied over the Drug Coat to at least partially coat the Drug Coat and form a Top Coat. The coatings have a total thickness of less than 100 μm, preferably less than 50 μm and most preferably, less than 25 μm.

The first polymeric solution (forming the Drug Coat) is formed by dissolving a first set of solids comprising a first set of polymers and one or more therapeutic agents, e.g., paclitaxel, in a suitable solvent or solvent mixture. The weight percentage of the solids in the solvent is in the range of about 0.1 to about 10 weight percent, more preferably from about 1 to about 5 percent. A polymer solution is formed in the solvent and the one or more therapeutic agents, such as paclitaxel is added to the polymer solution. Any suitable unreactive organic solvent or mixture of such solvents may be used in the present invention, including dichloromethane (DCM), ethyl acetate, acetone, methyl tert-butyl ether, toluene, or 2-methyltetrahydrofuran, for example. The first polymer solution is preferably made from a biodegradable polymer or mixture of such polymers admixed with the therapeutic agent(s) such that the therapeutic agent is eluted from the polymeric coating over time, or is released from the coating as it degrades in-vivo. The first set of solids of the polymer solution may comprise PLCL and PLA and paclitaxel, for example. In certain embodiments, the solids of the first solution comprise from 10 to 99 weight percent PLCL, 1 to 90 weight percent PLA, and from 0.05 to 20, preferably 0.1 to 20, 0.05 to 10, 2 to 5 or 3 to 4 weight percent of paclitaxel.

The optional, second biodegradable polymeric solution (forming the Top Coat) is similarly formed by dissolving a second set of solids comprising a second set of polymers, which may be the same or different from the first set of polymers of the first solution, in a suitable solvent or solvent mixture. In some embodiments, the second polymeric solution may contain therapeutic agent, such as paclitaxel. As with the first solution, any suitable unreactive organic solvent or mixture of such solvents may be used, including dichloromethane (DCM), ethyl acetate, acetone, methyl tert-butyl ether, toluene, or 2-methyltetrahydrofuran. In one embodiment, the second set of solids comprises PLCL and PLA. In a preferred embodiment, the solids of the second coating solution comprise from 10 to 99 weight percent PLCL and 1 to 90 weight percent poly lactic acid. The weight percentage of the second set of solids in the solvent is in the range of from 0.1 to 5, and preferably from 0.5 to 2 weight percent.

In preferred embodiments, the first polymeric solution and second polymeric solution are admixtures of PLCL and PLA. In such embodiments, the weight ratio of PLCL to PLA in the first and second polymeric solutions ranges from 15:85 to 35:65, preferably 20:80 to 30:70, 40:60 to 60:40, 45:55 to 55:45 or 50:50.

The specific polymeric formulations of the first solution and second solution are adjusted as described herein above to provide the desired type and amount of each polymer or polymer blend and therapeutic agent.

The Drug Coat and optional Top Coat may be applied to one or more or all of the strands of the implant body by any suitable method, such as dip-coating, spray coating, electrospraying or chemical vapor deposition. The Drug Coat is applied directly to the metallic strand(s), to conformally coat at least a portion of the tubular body. The optional Top Coat, which may also contain therapeutic agent, acts to regulate the delivery of the therapeutic agent from the Drug Coat into bodily tissue. When present, the Top Coat is applied to at least a portion of the Drug Coat to conformally coat at least a portion of the Drug Coat.

The Drug Coat is applied directly to the tubular body by spray coating the first polymeric solution containing the therapeutic agent(s), for example. Preferably, the tubular body is rotated along its longitudinal axis while the coating solution is sprayed or otherwise applied thereon. The coating thickness may be controlled by the spray time and speed of rotation, for example. Following the application step, heat is applied to the coating at a temperature and amount of time to cause substantially all of the solvent in the Drug Coat solution to evaporate, thereby providing a dry coating.

In those embodiments where a Top Coat is applied to the inventive stent, it is applied to at least a portion of the Drug Coat after the solvent in the Drug Coat has been sufficiently evaporated, preferably by spraying onto at least a portion of the Drug Coat. The Top Coat may be applied while the tubular body is rotated along its longitudinal axis. The coating thickness of the Top Coat may be controlled by the spray time and speed of rotation, for example.

In those embodiments where a Top Coat is applied to the inventive stent, heat is applied to the coating at a temperature and amount of time to cause substantially all of the solvent in the Top Coat solution to evaporate and dry the Top Coat.

When present, the Top Coat acts as a diffusion barrier such that the rate of delivery of the therapeutic agent(s) from the Drug Coat and is limited by the rate of its diffusion through the Top Coat. The thickness of the Top Coat and underlying Drug Coat affect the drug elution rate. In order to obtain the desired drug elution rate and maintain patency of the stent coatings during deployment and recovery, the total thickness of the coatings applied to the tubular body is generally less than 100 microns, and preferably less than 50 microns, more preferably less than 25 microns. More particularly, the ratio of thickness of the Drug Coat to that of the Top Coat is generally in the range of 1 to 4, and in certain embodiments from 1.25 to 3.75, from 1.25 to 2.5 or 1.5 to 2, for example.

The thickness of each polymer coating applied to the metallic stent body may be varied based on the specific composition of the polymer materials in each coating. For example, Drug Coat and Top Coat each comprising PLCL and PLA (15:85 to 35:65 weight %) may be applied at a thickness ratio of from 1.25 to 2.5, or from 1.5 to 2.0 (Drug Coat to Top Coat) to obtain an elution profile of drug, e.g., paclitaxel, based on the total amount of drug in the stent, of from 1.0 to 6% each week from 6 weeks to 20 weeks, as measured by submersion of the stent in a pH 7.4 phosphate-buffered saline buffer solution containing 2 wt % sodium dodecyl sulfate at 37° C. under action of a rotary shaker, and replacing the buffer solution with fresh buffer weekly for quantification. A similar paclitaxel elution rate may be obtained, for example, by application of a Drug Coat and Top Coat comprising PLCL and PLA in each coating (40:60 to 60:40) at a thickness ratio of 1.25 to 3.75, or from 2 to 3 (Drug Coat to Top Coat).

The inventors have surprisingly found that it is possible to achieve substantial structural integrity of the coatings on the stent body with the inventive coated metallic stents, including at the points of intersections of any overlapping strands or overlapping strand portions, even after lengthening to up to 200% of the original length of the tubular body, followed by shortening to substantially the original (as-manufactured) length as occurs during deployment of the device into a body lumen. Coating integrity is maintained following simulated deployment via a 6 Fr or 7 Fr catheter system, for example.

The devices of the invention have a combination of structure and composition that provides them with exceptional expandability and mechanical properties when compared with conventional self-expanding devices, as well as exceptional drug elution properties, as described herein.

In another aspect, the present invention provides a method of treating a subject, such as a mammal, comprising delivering a coated medical implant of the invention to a target site within a body lumen of a subject in need of treatment. In an embodiment of this aspect, the medical implant delivers a therapeutic agent, such as paclitaxel, at the target site in a controlled release manner. In preferred embodiments, the coated medical implant releases the amount of therapeutic agent released at or near the target site ranges from 0.3 ng/mm$^2$ to 2.5 ng/mm$^2$ of the surface area of the stent per day over a period of time from 5 days to 180 days of submersion in a pH 7.4 phosphate-buffered saline buffer solution containing 2 wt % sodium dodecyl sulfate at 37° C. under action of a rotary shaker, when the buffer solution is removed completely weekly for paclitaxel quantification and replaced with fresh buffer solution.

The present invention is further described with reference to the following non-limiting examples.

Example 1

Several inventive metal drug eluting stents (MDES) were manufactured by applying a Drug Coat layer and a Top Coat layer on various commercially available bare metal stents (BMS) listed in Table 1 using a spray-coating method. Details of the spray-coating procedure are described below.

TABLE 1

Stent strut design and surface area of different BMS

| BMS | Strut width (μm) | Strut thickness (μm) | Stent mass (mg/10 mm) | Stent surface area (mm$^2$/10 mm) |
|---|---|---|---|---|
| Absolute Pro ™ | 110 | 230 | 33 | 135 |
| EverFlex ™ | 108 | 161 | 43 | 206 |
| LifeStent ® | 100 | 205 | 43 | 200 |
| S.M.A.R.T. ® Vascular | 100 | 173 | 44 | 215 |
| S.M.A.R.T. ® Flex | 75/100 | 170 | 31 | 172 |
| Supera ® | 174 | NA | 56 | 199 |

Coating Solution Preparation

Poly(L-lactide-co-ε-caprolactone) (PLCL, 1.45 g), poly (L-lactide) (PLA, 4.34 g), and paclitaxel (PTx, 0.21 g) were weighed using an analytical balance and transferred to a 250 mL wide mouth glass jar. Then, 140 mL dichloromethane (DCM) was added to completely dissolve the solid under gentle shaking. Thereafter, 60 mL anisole (AN) was combined to afford a homogenous DC solution of 3% wt/v solid in DCM/AN (7:3 v/v).

In the preparation of the TC solution, 1.0 grams of PLCL and 3.0 grams of PLA were dissolved in 400 mL DCM to give a TC solution of 1% wt/v.

Drug Coat Application

A Drug Coat layer was first applied onto the BMS. Typically, BMS were mounted on a holding fixture that was inserted horizontally into a rotating shaft within a coating apparatus. The coating apparatus was rotated on its axis and translated horizontally through the spray plume of the Drug Coat solution throughout an automated coating process. The transverse distance exceeded the length of the stent to ensure that the entire stent was uniformly coated. The coverage, or amount of coating applied, was controlled by the combination of the transverse speed and the number of passes through the spray plume.

The holding fixture supported the stent in an open configuration to allow a conformal coating of the individual stent struts. The Drug Coat solution was placed into the dispensing apparatus with an in-line filtration system in preparation for spray coating onto the surface of the stent. Although the coating was applied to the exterior or abluminal surface of the stent, spray solution also passed through the open cell structure to coat the interior surface of the struts, resulting in a complete conformal coating of the stent.

After coating, the stents were dried at 70° C. in a convection oven for 16 h to allow the complete evaporation of the solvents. Stent mass was recorded before and after applying the Drug Coat. The mass of the Drug Coat layer was determined by the mass difference.

Top Coat Application

Top Coat solution was spray-coated onto the Drug-Coated stents according to the procedure described above for application of the Drug Coat. After application of the Top Coat, the stents were dried at 70° C. Stent mass was recorded after applying the Top Coat to assess the mass of the Top Coat layer.

Inventive formulations of the Drug Coat and Top Coat were coated onto a number of commercially available bare metal stent (BMS) platforms as described above and drug elution profiles were obtained. The MDES that is obtained by coating the EverFlex®, Lifestent®, S.M.A.R.T.® Vascular, and Supera® stents exhibit comparable KDR profiles when the same DC/TC coatings are employed although they have considerably different stent designs. Table 1 above compares the strut dimension, stent mass, and stent surface area of these BMS.

Example 2

Absolute Pro® Platform

The viability of the drug coatings on metal stents was tested on the platform of the Absolute Pro® stent (ID=7 mm) (Abbott Laboratories, Abbott Park, Ill.). PLCL was used as the Drug Carrier and PLCL/PLA (75:25 wt:wt) as the Top Coat (Table 1). The coating mass was 2 mg/10 mm for DC and 0.8 mg/10 mm for TC (Exp078), respectively. An MDES with thicker TC (Exp078B) was also fabricated to evaluate the impact of TC thickness on PTx drug release. To achieve a total PTx loading of 35 μg/10 mm, the PTx loading rate in the DC layer was maintained at 1.75 wt %.

TABLE 2

PTx coated Abbott Absolute Pro ® stents.

| Group | PTx in DC (wt %) | DC polymer | DC mass (mg/10 mm) | TC polymer | TC mass (mg/10 mm) | PTx loading (μg/10 mm) |
|---|---|---|---|---|---|---|
| Exp076 | 1.75 | PLCL | 2.0 | NA | NA | 35 |
| Exp078 | 1.75 | PLCL | 2.0 | PLCL/PLA (75:25) | 0.8 | 35 |
| Exp078B | 1.75 | PLCL | 2.0 | PLCL/PLA (75:25) | 2.0 | 35 |

Note:
mg/10 mm refer to mg of material per 10 mm of stent length

Figure 3:
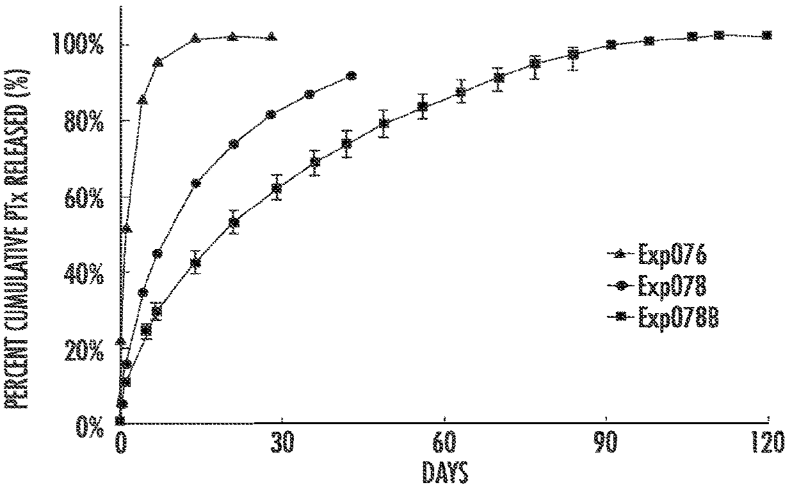
FIG. 3 is a graph showing the cumulative percent mass of Paclitaxel (PTx) released from various drug coated Absolute Pro-based stents as a function of time.

The in vitro kinetic drug release (KDR) profiles of these PTx coated stents were assessed using pH 7.4 PBS with 2% SDS as an elution medium. A drug coated stent was placed in a vial containing a specific amount of PBS-SDS solution that ensures infinite drug sink conditions. The vial was incubated in a water bath at 37° C. under gentle agitation. At predetermined sampling time points, the elution medium was withdrawn and the PTx eluted from the stent measured using HPLC-UV. Fresh elution medium was added to maintain the infinite sink conditions. FIG. 3 illustrates the KDR release profiles of these PTx coated stents.

The KDR of stents with TC (Exp078) is slower than that of stents without TC (Exp076).

Figure 4A:
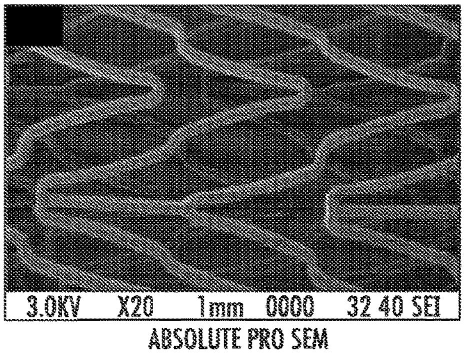
FIG. 4A and FIG. 4B are (FIG. 4A) Low and (FIG. 4B) high magnification scanning electron micrograph (SEM) images of DC/TC coated Absolute Pro® MDES014 post simulated deployment using a 7.5 Fr catheter.
Figure 4B:
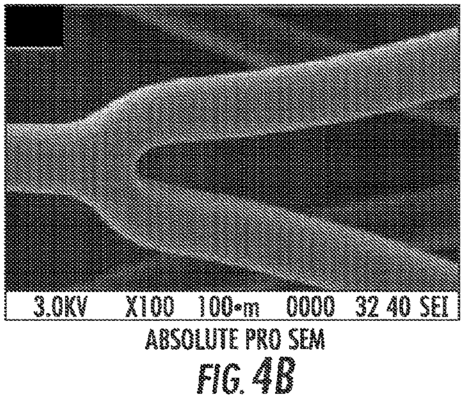

Another DC/TC formulation was applied onto the Absolute Pro stent (MDES014). The DC layer carries 0.875 wt % PTx and the remainder of PLCL/PLA (50:50), while the TC layer is a drug-free blend of PLCL and PLA at 50:50 ratio. The mass of the DC and TC layers are 4 mg/10 mm and 2 mg/10 mm, respectively. The SEM images of the coated stents post-simulated deployment using a 7.5 Fr catheter are shown in FIG. 4. No obvious defects, such as coating wrinkling, fracture, cracking, or missing, were observed in the stents post-simulated deployment.

Figure 5:
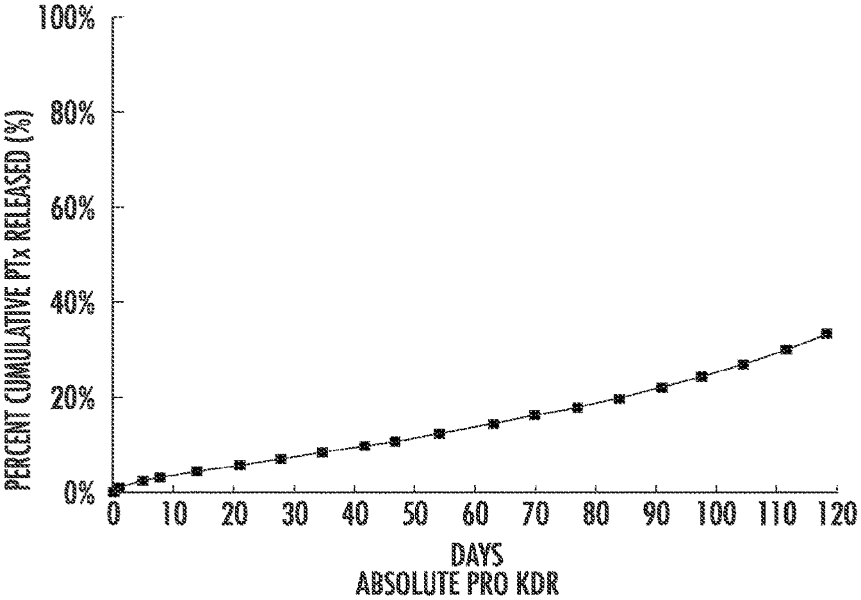
FIG. 5 is a graph of the cumulative percent mass of PTx released from MDES014 as a function of time.

The KDR profile of DC/TC coated Absolute Pro® MDES014 post simulated deployment is shown in FIG. 5.

Example 3

EverFlex® Platform

The EverFlex® peripheral vascular stent was used as a platform to develop a drug coating that can deliver PTx up to 6 months. PLCL and D,L-PLGA (85:15) (Polymer reference #RG858 S) were respectively used as the drug carrying polymers, while PLCL/PLA (75:25 wt:wt) was used as the TC layer. Details of the coating composition and coating mass of DC and TC layers on these stents are summarized in Table 3.

TABLE 3

Coating formulations on EverFlex ® stents

| Group | PTx in DC (wt %) | DC polymer | DC mass (mg/10 mm) | TC polymer | TC mass (mg/10 mm) | PTx loading (μg/10 mm) |
|---|---|---|---|---|---|---|
| Exp 085C | 0.875 | PLCL | 4.0 | PLCL/PLA (75:25) | 2.0 | 35 |

TABLE 3-continued

| Coating formulations on EverFlex ® stents | | | | | | |
|---|---|---|---|---|---|---|
| Group | PTx in DC (wt %) | DC polymer | DC mass (mg/10 mm) | TC polymer | TC mass (mg/10 mm) | PTx loading (μg/10 mm) |
| Exp 085D | 0.875 | PLCL | 4.0 | PLCL/PLA (75:25) | 4.0 | 35 |
| Exp 085B | 0.875 | RG858 S | 4.0 | NA | NA | 35 |
| Exp 085E | 0.875 | RG858 S | 4.0 | PLCL/PLA (75:25) | 2.0 | 35 |

Note:
mg/10 mm refer to mg of material per 10 mm of stent length

Figure 6:
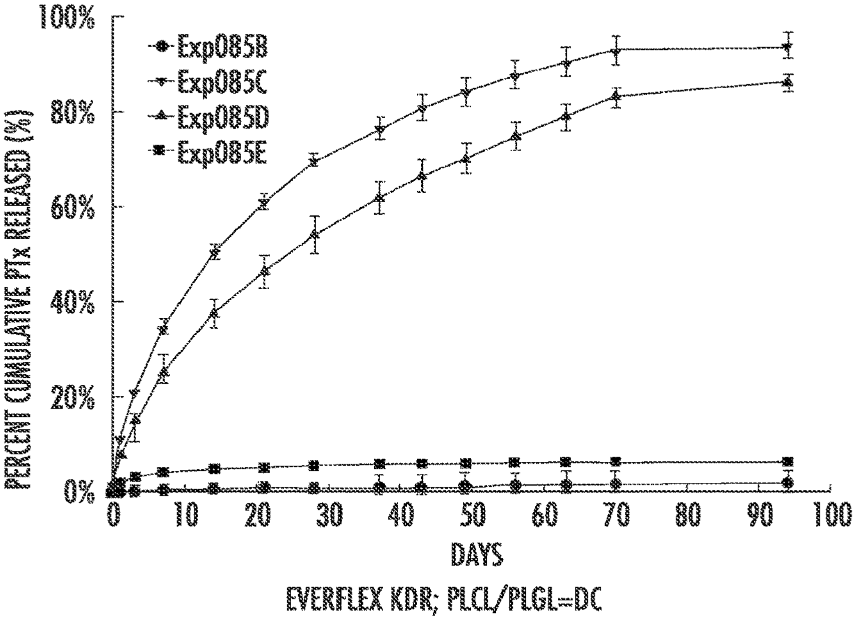
FIG. 6 is a graph showing the cumulative percent mass of PTx released from drug coated EverFlex® Exp085B-E as a function of time.

Stents Exp 085B to Exp 085E were subject to KDR evaluation without simulated deployment. FIG. 6 shows their KDR profiles over a period of 94 days. Both Exp 085C and Exp 085D carry the same DC layer of PLCL and PTx, but their TC layers have different thickness.

With RG858 S as the drug carrier, PTx was trapped in the polymer matrix and had a very slow KDR rate (FIG. 6). The top coated stent Exp085E shows slightly faster burst release than the stent with only a DC layer (i.e., Exp 085B). It is possible that a certain level of mixing occurs between the DC and the TC layers that contains PLCL, which enables the observed faster burst release of PTx.

A blend of PLCL and PLA at 50:50 wt:wt ratio was further used as the drug carrier to form the DC layer. As compared with the prior coatings, the PLA content is significantly increased. The same polymer blend was also used as the TC layer. The details on the coating formulations, including the PTx loading and the mass of DC/TC layers, are summarized in Table 4.

TABLE 4

| PLCL/PLA(50:50)-based coating formulations on EverFlex ® stents | | | | | | |
|---|---|---|---|---|---|---|
| Group | PTx in DC (wt %) | DC polymer | DC mass (mg/10 mm) | TC polymer | TC mass (mg/10 mm) | PTx loading (μg/10 mm) |
| Exp098A | 0.875 | PLCL/PLA (50:50) | 4.0 | NA | NA | 35 |
| Exp098B | 0.875 | PLCL/PLA (50:50) | 4.0 | PLCL/PLA (50:50) | 2.0 | 35 |

Note:
mg/10 mm refer to mg of material per 10 mm of stent length

SEM images of Exp 098A and Exp 098B confirmed that a conformal coating was obtained on both DC and DC/TC coated stents.

Figure 7A:
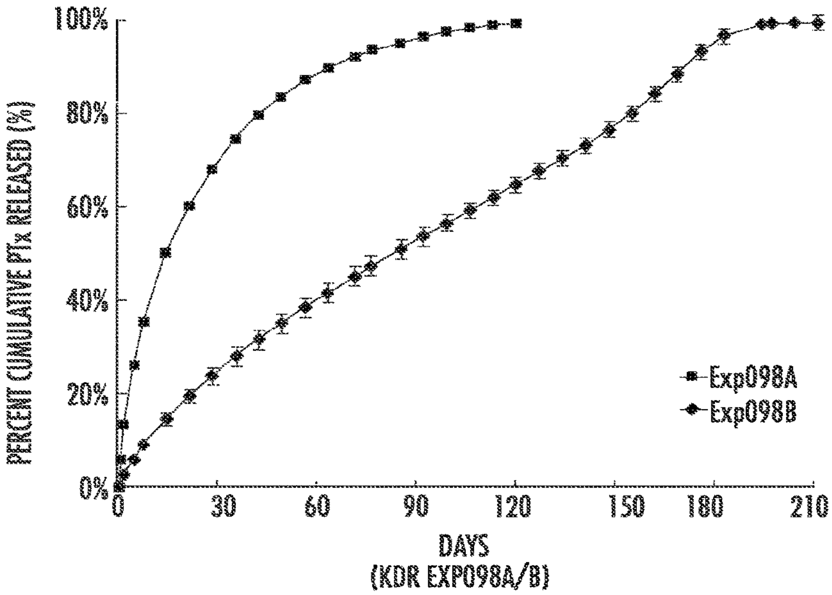
FIG. 7A and FIG. 7B are graphs showing elution of drug.

The KDR profiles of as coated (i.e., not sim deployed) Exp 098A and Exp 098B were recorded and shown in FIG. 7*a*. Stent Exp 098A releases PTx up to 4 months, but with high burst release at the early stage. In the case of Exp 098B, a near linear PTx release profile is obtained and the drug release duration was extended to 6 months. Slightly faster PTx release is observed between 5 to 6 months, which is most likely due to the degradation of the coating polymers. About 8% polymer mass loss was observed at 220 days.

Figure 7B:
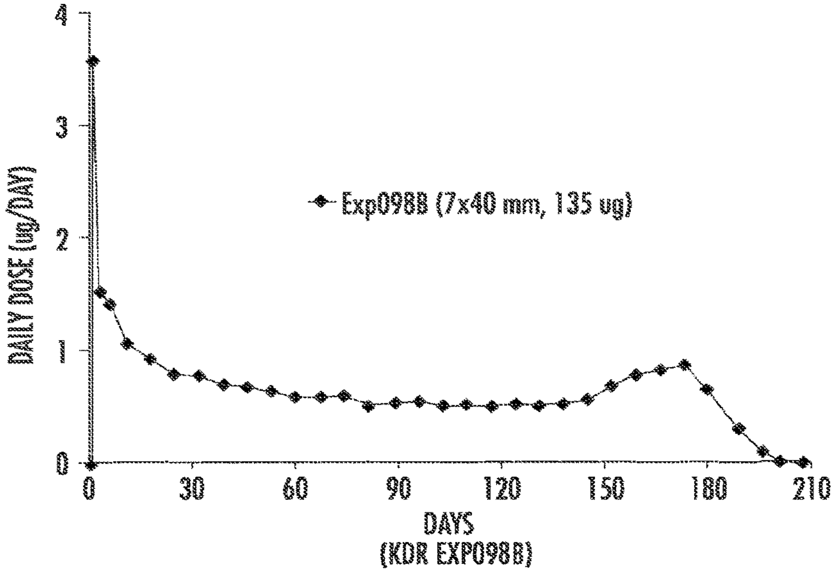

The daily dose release of stent Exp 098B was plotted as a function of time in FIG. 7*b*, where the drug loading is normalized to a stent of 7 mm (D)×40 mm (L) and the total drug loading in the stent is 135 μg. The burst release of PTx within the first 24 h was only 3.6 μg (i.e. 2.7%). From Day 1 to Day 14, the daily dose was about 1.0 to 1.5 μg/day. From Day 15 to Day 180, the daily dose was about 0.5 to 1.0 μg/day, confirming a consistent PTx release from the corresponding coated stents.

Example 4

Impact of Simulated Deployment on Coating Morphology and Kinetic Drug Release (KDR)

Because PLA is a non-elastic polymer, its incorporation into the coating layers reduces the elasticity of the entire coating. MDES stent MDES002A, which has the following Drug Coat and Top Coat was subjected to simulated deployment using a 7.5 Fr catheter:

PTx in Drug Coat (wt %): 0.875
Drug Coat Polymer: PLCL/PLA (50:50)
DC mass (mg/10 mm): 4.0
Top Coat polymer: PLCL/PLA (50:50)
Top Coat mass (mg/10 mm): 2.0
PTx loading (μg/10 mm): 35
(mg/10 mm refers to mg of material/10 mm of stent length)

Figure 8A:
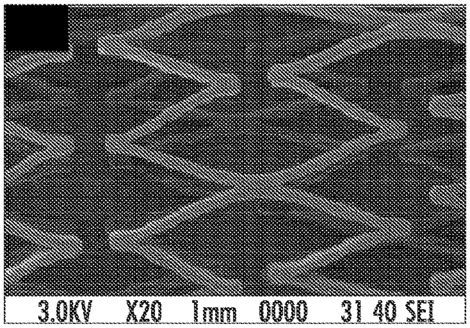
FIGS. 8A and 8B are (FIG. 8A) Low and (FIG. 8B) high magnification SEM images of drug coated EverFlex® stent MDES002A post simulated deployment using a 7.5 Fr catheter.
Figure 8B:
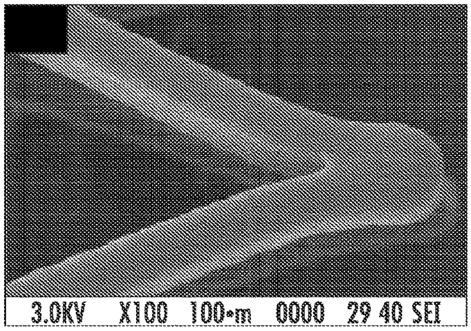

FIGS. 8*a* and 8*b* show low and high magnification SEM images of the stent post simulated deployment. No coating delamination or ruptures were observed, confirming the robustness of the coating materials.

Figure 9:
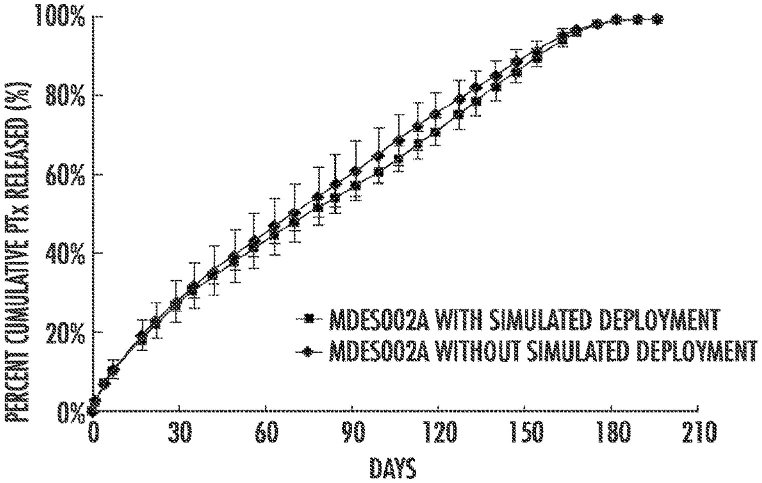
FIG. 9 is a graph showing cumulative percent mass of PTx released from drug coated EverFlex® MDES002A with and without simulated deployment as a function of time. For crimped stents a 7.5 F Catheter was used to deploy the stents.

The KDR profiles of MDES002A with and without simulated deployment were recorded and the corresponding results are shown in FIG. 9. As can be seen, both stents display essentially identical KDR profiles.

Figure 10:
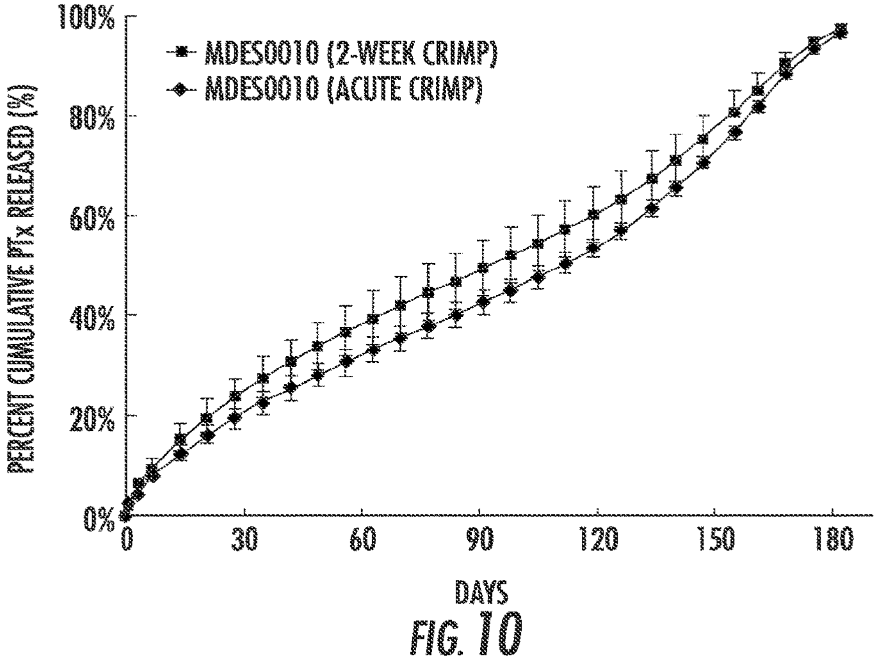
FIG. 10 is a graph showing cumulative percent mass of PTx released from drug coated EverFlex® MDES010 as a function of time. The stents were subject to a 10 minute or 2-week crimp in a 7.5 Fr catheter prior to deployment.

The impact of long-term stent crimp on the drug elution profile was also evaluated. MDES010 stents carrying PLCL/PLA (50:50)-based drug coating formulations (Coating thickness ~24 μm) were crimped using a hand-held crimper and transferred into a 7.5 Fr catheter and maintained at the crimped status for 10 min and 2 weeks, respectively. The stents were immersed in 37° C. water for 10 min before being deployed in the water. No significant difference was observed for the KDR profiles of these two stents (FIG. 10). In addition, stents crimped in a 7.5 Fr catheter for up to 4 weeks showed no coating defects after deployment (SEM images not shown). These results indicate that the coated stents can be crimped for extended period of time without impacting performance.

Example 5

Reduction of Material Burden

Although the Exp 098B coating formulations may provide drug release for up to 6 months duration, the material burden of the coated stents is relatively high (6 mg/10 mm). High coating mass may increase difficulties in loading the coated stent into catheters of smaller size (e.g., 6 Fr). Therefore, attempts were made to reduce the polymer burden while preserving the 6-month release profile. The formulations that have been evaluated on the EverFlex® stent are compiled in Table 6.

TABLE 5

PLCL/PLA (50:50)-based coating formulations that have lower material burden than MDES002A (i.e., 6 mg/10 mm).

| Group | PTx in DC (wt %) | DC polymer composition | DC mass (mg/10 mm) | TC polymer composition | TC mass (mg/10 mm) | PTx loading (μg/10 mm) |
|---|---|---|---|---|---|---|
| MDES002A | 0.875 | PLCL/PLA (50:50) | 4.0 | PLCL/PLA (50:50) | 2.0 | 35 |
| MDES002B | 3.5 | PLCL/PLA (50:50) | 1.0 | PLCL/PLA (50:50) | 2.0 | 35 |
| MDES004A | 1.75 | PLCL/PLA (50:50) | 2.0 | PLCL/PLA (50:50) | 2.0 | 35 |
| MDES004B | 1.75 | PLCL/PLA (50:50) | 1.0 | PLCL/PLA (50:50) | 2.0 | 17.5 |

Note:
mg/10 mm refer to mg of material per 10 mm of stent length

Figure 11:
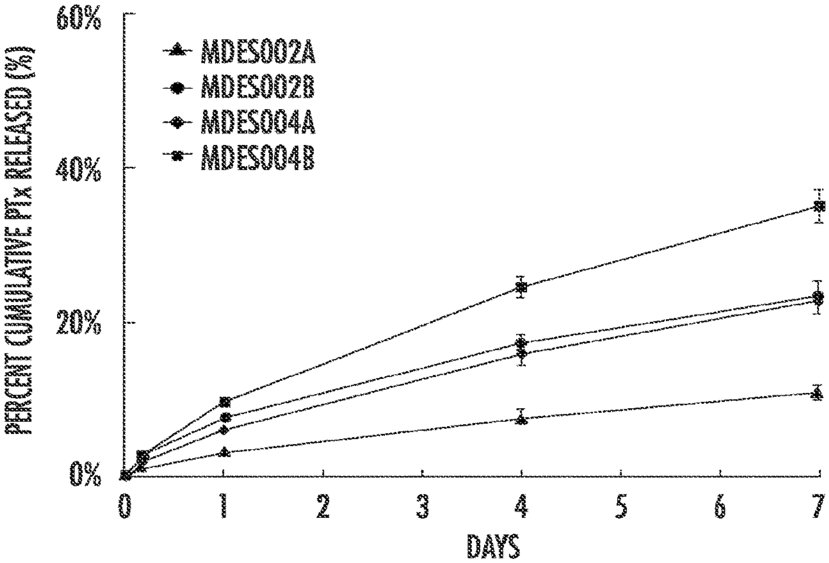
FIG. 11 is a graph showing cumulative percent mass of PTx released from various drug coated EverFlex® stents as a function of time.

The 7-day KDR profiles of these stents are plotted in FIG. 11. As compared with the baseline group (MDES002A), the other 3 groups of stents possess the same TC layer, but a thinner DC layer. All 3 groups have a faster KDR than the baseline group, suggesting that the DC layer has an impact on the drug release rate. The drug diffusion path is shortened along with a reduction in the thickness of the DC layer.

FIG. 11 also shows that the drug release from MDES004B is much faster than that from MDES002B, although they carry the same DC and TC masses. The only difference for these two groups of stents is the loading rate of PTx in the DC layer. MDES002B has a PTx loading rate of 3.5% in the DC layer, while MDES004B has a loading rate of 1.75%.

Example 6

LifeStent® Platform: PLCL/PLA (50:50)-Based Formulation

Figure 12A:
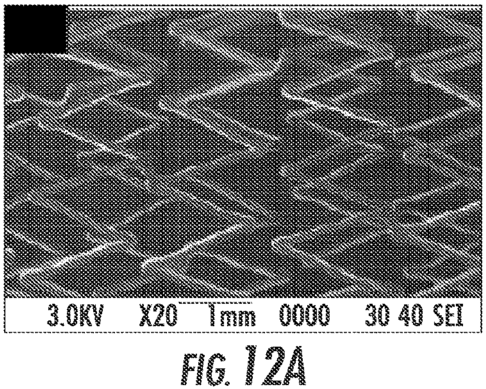
FIG. 12A, FIG. 12B, FIG. 12C and FIG. 12D are SEM images of (FIG. 12A) bare LifeStent®, (FIG. 12B) as coated MDES007, (FIG. 12C) MDES007 post simulated deployment, and (FIG. 12D) the stent of (FIG. 12C) under high magnification.
Figure 12B:
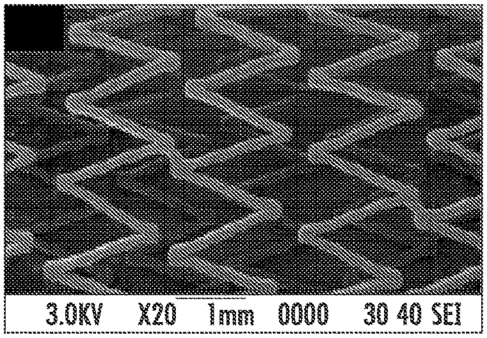
Figure 12C:
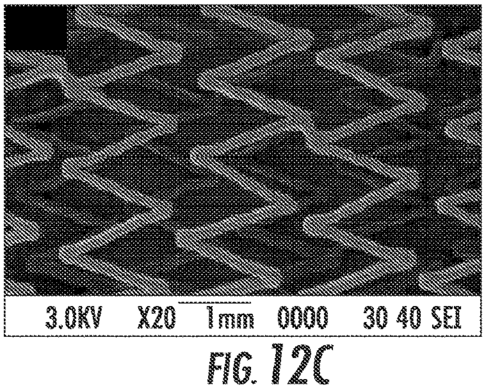
Figure 12D:
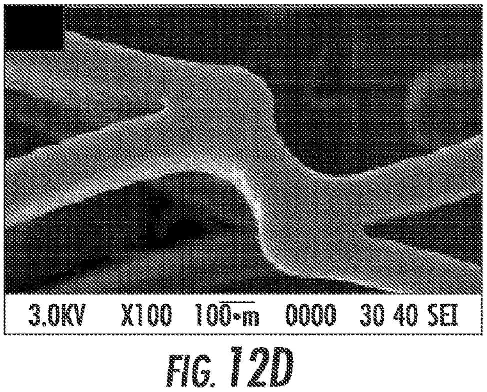

A PLCL/PLA (50:50)-based DC/TC formulation of 6 month PTx release duration was coated onto the LifeStent® stent (Table 6). The LifeStent stent has unique helical struts and angled bridges (FIG. 12*a*). The spray coating process applies conformal DC and TC layers onto the struts of LifeStent® stents (FIG. 12*b*). After simulated deployment using a 7.5 Fr catheter, the coating layers remain intact (FIGS. 12*c* and 12*d*), once again confirming the durability of the coating formulation.

TABLE 6

PLCL/PLA(50:50)-based coating formulations on EverFlex ® and LifeStent ® stents.

| Group | BMS platform | PTx in DC (wt %) | DC polymer composition | DC mass (mg/10 mm) | TC polymer composition | TC mass (mg/10 mm) | PTx loading (μg/10 mm) |
|---|---|---|---|---|---|---|---|
| MDES002A<br>MDES007 | EverFlex ®<br>LifeStent ® | 0.875 | PLCL/PLA (50:50) | 4.0 | PLCL/PLA (50:50) | 2.0 | 35 |

Note:
mg/10 mm refer to mg of material per 10 mm of stent length

Figure 13:
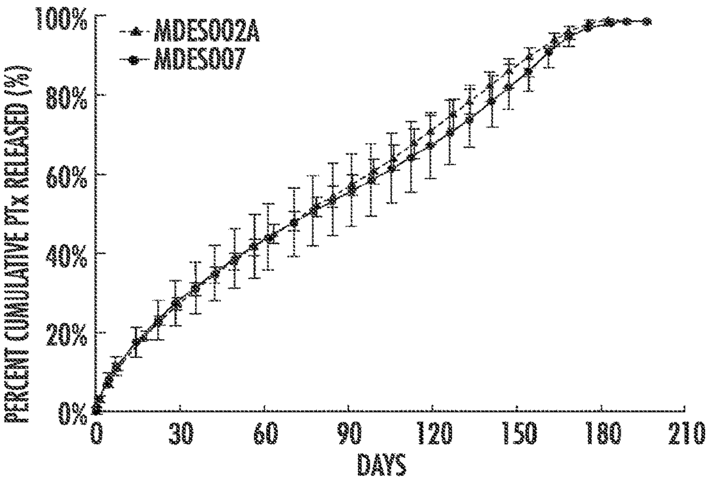
FIG. 13 is a graph showing the in vitro kinetic drug release (KDR) profiles of PTx coated LifeStent® stents compared to the EverFlex® stent. All were coated with the same DC/TC coating formulation (i.e. 35 μg PTx/10 mm length).

FIG. 13 illustrates the KDR profile of a PTx coated LifeStent® stent (MDES007). For the purpose of comparison, the KDR profile of EverFlex®-based stent MDES002A is also plotted in FIG. 13. The stents were subject to KDR post simulated deployment using a 7.5 Fr catheter. The KDR profile of the LifeStent®-based MDES is essentially the same as that of the EverFlex®-based MDES with the same DC/TC coatings.

Example 7

Reduction of Material Burden

To reduce the material burden, new formulations were tested on the LifeStent® platform. The formulations are summarized in Table 7.

TABLE 7

Formulations to reduce material burden on the LifeStent ® stents.

| Group | PTx in DC (wt %) | DC polymer composition | DC mass (mg/10 mm) | TC polymer composition | TC mass (mg/10 m) | PTx loading (μg/10 mm) |
|---|---|---|---|---|---|---|
| MDES007 | 0.875 | PLCL/PLA (50:50) | 4.0 | PLCL/PLA (50:50) | 2.0 | 35 |
| MDES031 | 3.5 | PLCL/PLA (50:50) | 1.0 | PLCL/PLA (50:50) | 3.0 | 35 |
| MDES035 | 0.875 | PLCL/PLA (25:75) | 4.0 | PLCL/PLA (25:75) | 2.0 | 35 |
| MDES036A | 3.5 | PLCL/PLA (25:75) | 1.0 | PLCL/PLA (25:75) | 2.0 | 35 |
| MDES036B | 3.5 | PLCL/PLA (25:75) | 1.0 | PLCL/PLA (25:75) | 3.0 | 35 |
| MDES047A | 3.5 | PLCL/PLA (10:90) | 1.0 | PLCL/PLA (10:90) | 1.0 | 35 |
| MDES047B | 3.5 | PLA | 1.0 | PLA | 1.0 | 35 |

Note:
mg/10 mm refer to mg of material per 10 mm of stent length

Figure 14:
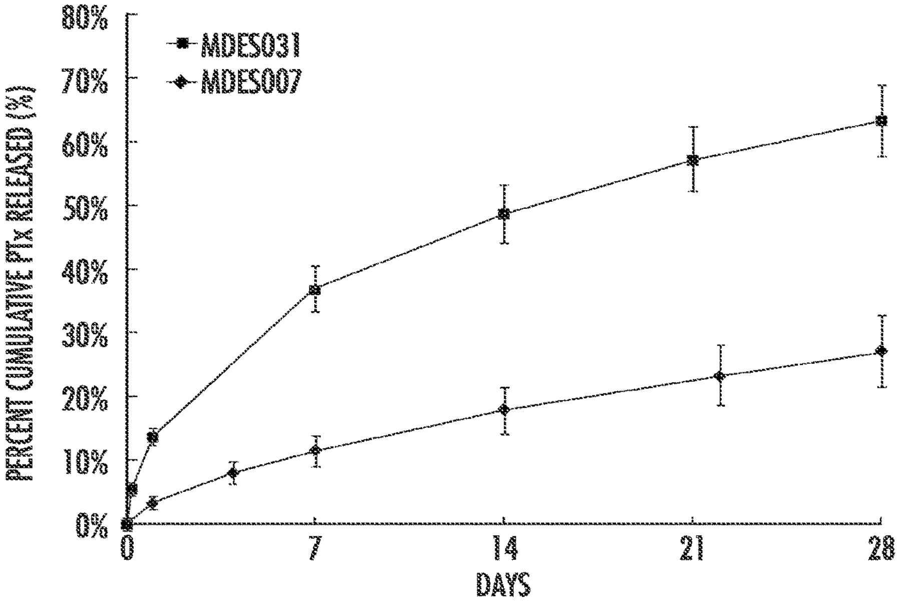
FIG. 14 is a graph showing cumulative percent mass of PTx released from MDES007 and MDES031 as a function of time.
Figure 15:
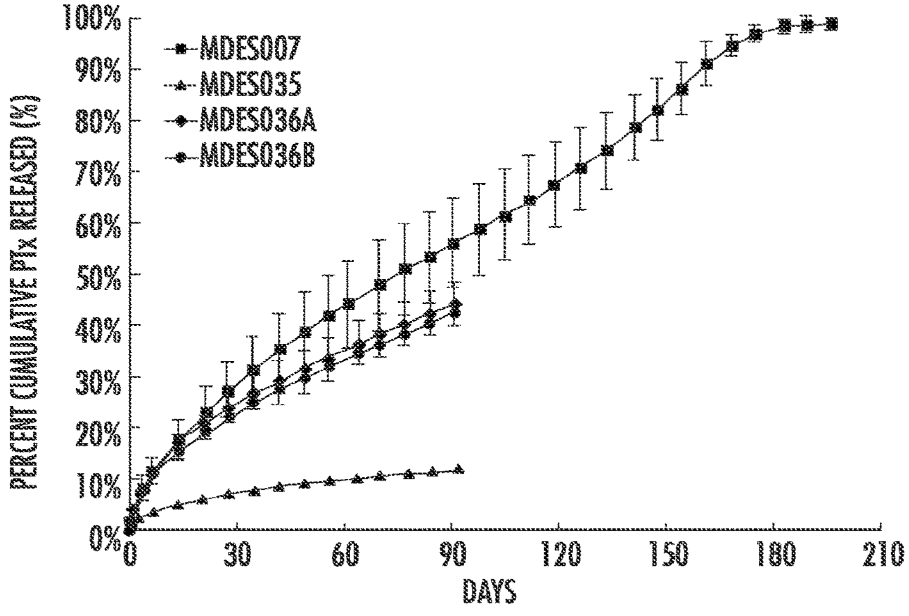
FIG. 15 is a graph showing cumulative percent mass of PTx released from coated LifeStent® stents as a function of time. PLCL/PLA (50:50 wt:wt) (MDES007) and PLCL/PLA (25:75) based formulations (MDES035 and MDES036A&B) are compared.
Figure 16A:
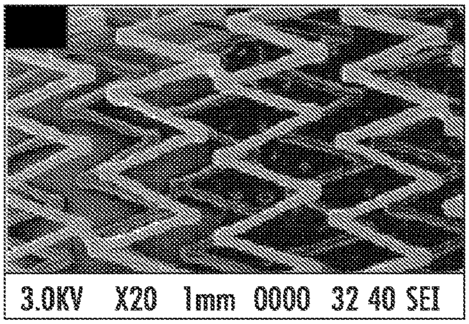
FIG. 16A, FIG. 16B, FIG. 16C and FIG. 16D are SEM images of MDES035 ((FIG. 16A) and (FIG. 16B)) and MDES036A ((FIG. 16C) and (FIG. 16D)), respectively, post simulated deployment in a 7.5 Fr catheter.
Figure 16B:
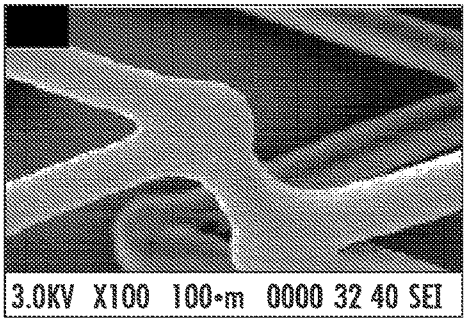
Figure 16C:
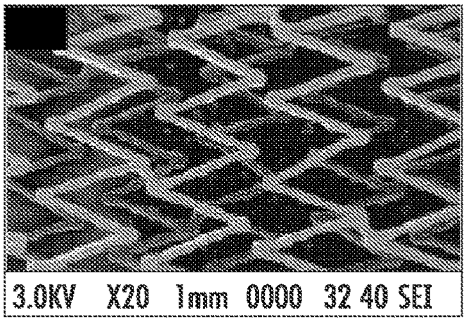
Figure 16D:
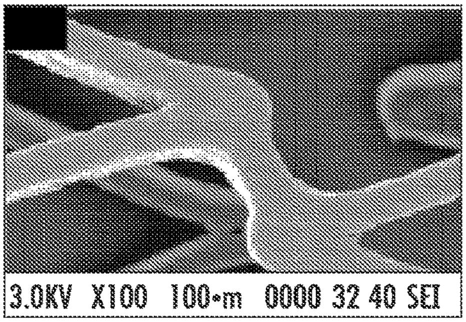
Figure 17A:
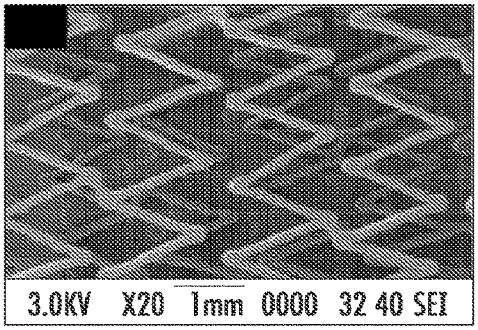
FIG. 17A, FIG. 17B, FIG. 17C and FIG. 17D are SEM images of MDESO47A ((FIG. 17A) and (FIG. 17B)) and MDESO47B ((FIG. 17C) and (FIG. 17D)), respectively, post simulated deployment in a 7.5 Fr catheter.
Figure 17B:
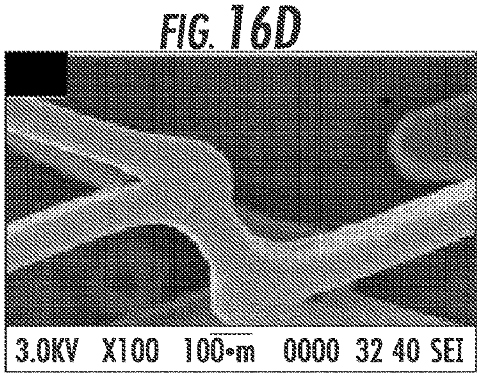
Figure 17C:
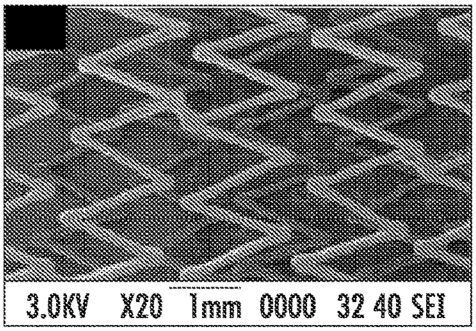
Figure 17D:
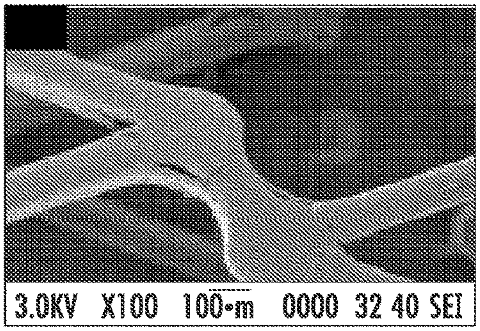

In a first trial, the TC mass was increased 50% in combination with a reduction of the DC mass by 75%. The overall reduction of DC/TC mass is about 33% as compared to the baseline. FIG. 14 shows the KDR profile of the stents with reduced coating mass (MDES031). The KDR rate was significantly faster than that of the baseline.

DC/TC formulations with higher PLA levels were coated onto the LifeStent® stent. Stents MDES035 and MDES007 share the same PTx loading rate and DC/TC coating mass, but the PLCL/PLA ratios in their DC/TC layers are 25:75 and 50:50, respectively. As can be seen from FIG. 14, the drug release rate is reduced by 70% when the PLA level increases from 50% to 75%, demonstrating the role of PLA in controlling the drug release rate.

Stents MDES036A and MDES036B were fabricated by reducing DC mass by 75%, while maintaining and increasing the TC mass by 50%, respectively, as compared with MDES035. As expected, both stents show faster KDR profiles than MDES035, which are comparable to the KDR of MDES007.

Example 8

Effect of Increasing PLA on Coating Integrity

The coating integrity of PLCL/PLA (25:75 wt:wt) based formulation post simulated deployment was evaluated to determine the effect of increased PLA content on coating integrity. The SEM images of MDES035 and MDES036A post simulated deployment using a 7.5 Fr catheter are depicted in FIG. 16. No significant coating defects were detected with either stent, indicating that the polymer blend is elastic enough to withstand simulated deployment conditions.

To explore the durability of PLCL/PLA blends at higher PLA levels, DC/TC layers containing PLCL/PLA (10:90) and pure PLA were coated onto LifeStent® stents, respectively. The details on the coatings are listed in Table 8. The SEM images of the MDES post simulated deployment using a 7.5 Fr catheter are shown in FIG. 17. As can be seen, the coatings based on PLCL/PLA (10:90) remain intact post simulated deployment. No cracking, delamination, or ripping of the coating was observed for MDESO47A. Some minor wrinkles were present on the surface of the stents post simulated use. When PLA was used as the sole coating polymer, numerous coating cracks were observed for the stents post simulated use. In the current system, 10% PLCL is the minimum requirement for the PLCL component to prevent surface cracking upon simulated use of the coated stents.

Figure 18:
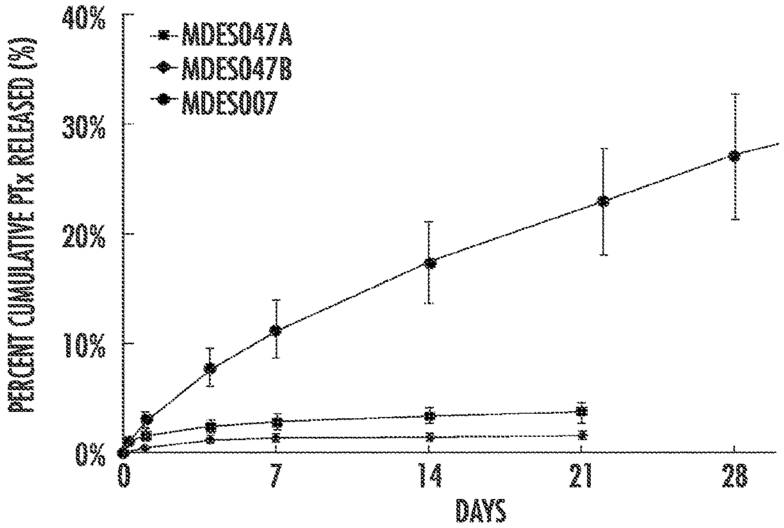
FIG. 18 is a graph showing cumulative percent mass of paclitaxel released from coated Lifestent® stents MDESO47A&B as a function of time.
Figure 19A:
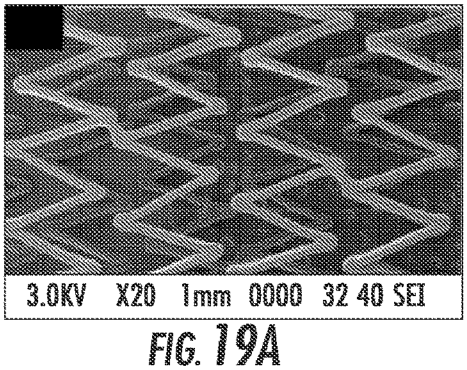
FIG. 19A, FIG. 19B, FIG. 19C and FIG. 19D are SEM images of MDES053A (7 mm LifeStent®, (FIG. 19A) and (FIG. 19B)) and MDES053B (6 mm LifeStent®, (FIG. 19C) and (FIG. 19D)) post simulated deployment of the respective stents using a 6 Fr catheter.
Figure 19B:
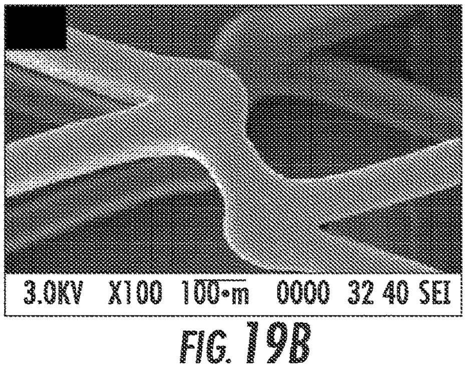
Figure 19C:
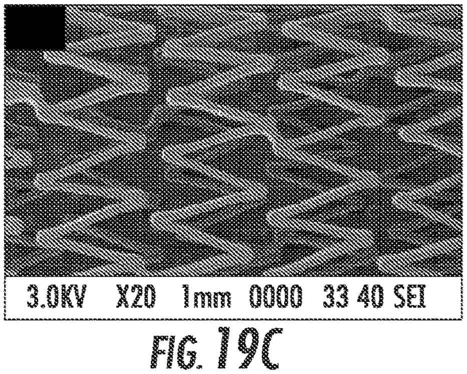
Figure 19D:
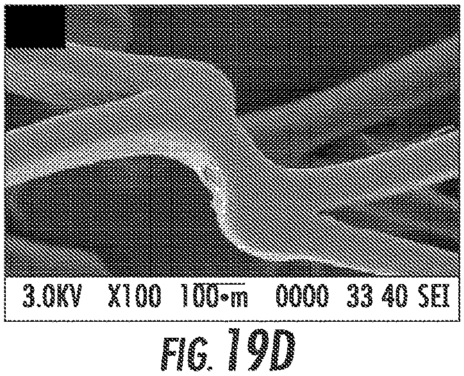

The KDR profiles of MDESO47A and MDESO47B were recorded and compared with that of MDES007 (FIG. 18). MDESO47A was subject to simulated use prior to the KDR measurement, while MDESO47B was used as-manufactured in the KDR study to eliminate the impact of coating damage. It was observed that both stents exhibit a slow drug release rate and there is essentially no drug released beyond the initial burst release phase.

Example 9

Compatibility of Coated LifeStent® Stents with 6 Fr Catheter

As demonstrated above, the coated stents of the invention can be delivered using a 7.5 Fr catheter with minimal impact on the coating integrity and KDR profiles. The compatibility of the coated stents with a 6 Fr catheter (ID=1.7 mm) was also analyzed using LifeStents® coated with the PLCL/PLA (50:50)-based formulations and a total DC/TC mass of 6 mg/10 mm. The results showed that these stents are not compatible with a 6 Fr catheter based on the combined thickness of the DC/TC coating. It was not possible to crimp these stents to 1.7 mm using a hand-held crimper. The LifeStent® stents coated with the PLCL/PLA (25:75) formulations and a total DC/TC mass of 3 mg/10 mm, however, were loaded into a 6 Fr catheter using a hand-held crimper. The LifeStent® stents of two diameters (6 & 7 mm) were coated with the formulations and tested. Table 8 summarizes the details on the coatings.

TABLE 8

Coated LifeStent ® stents subjected to 6 Fr catheter compatibility test

| Group | LifeStent ® Diameter (mm) | PTx in DC (wt %) | DC polymer composition | DC mass (mg/10 mm) | TC polymer composition | TC mass (mg/10 mm) | PTx loading (μg/10 mm) |
|---|---|---|---|---|---|---|---|
| MDES053A | 7 | 3.5 | PLCL/PLA | 1.0 | PLCL/PLA | 2.0 | 35 |
| MDES053B | 6 | | (25:75) | | (25:75) | | |

Note:
mg/10 mm refer to mg of material per 10 mm of stent length

FIG. 19 shows the SEM images of the coated 7 mm LifeStent® stents (MDES053A) and 6 mm LifeStent® stents (MDES053B) post simulated deployment using a 6 Fr catheter. Both stents show good coating integrity post simulated use in a 6 Fr catheter. Some minor defects were observed for the tested stents, which may be a result of crowded strut packaging or the high friction between the crimped stents and the catheter.

Figure 20:
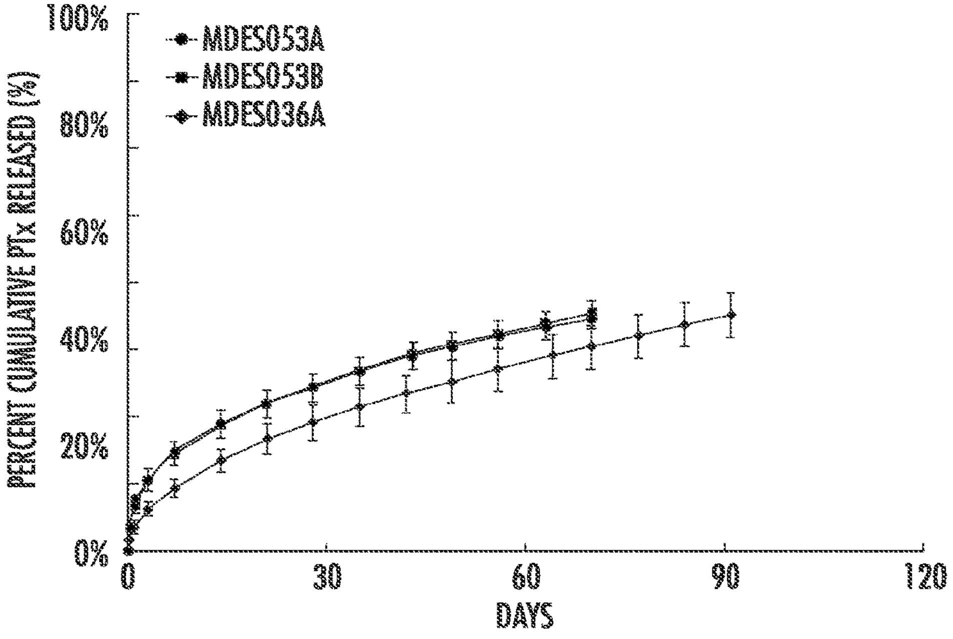
FIG. 20 is a graph showing the KDR profiles of coated LifeStent® stents. Stents MDES053A (7 mm) and MDES053B (6 mm) were deployed using a 6 Fr catheter, while stent MDES036A (7 mm) was deployed using a 7.5 Fr catheter.
Figure 21A:
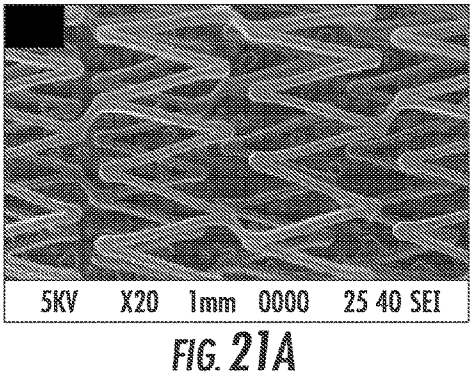
FIG. 21A, FIG. 21B, FIG. 21C and FIG. 21D are SEM images of MDES056B (6 mm S.M.A.R.T.® Vascular, (FIG. 21A) and (FIG. 21B)) and MDES056C (6 mm S.M.A.R.T.® Flex, (FIG. 21C) and (FIG. 21D)) post simulated.
Figure 21B:
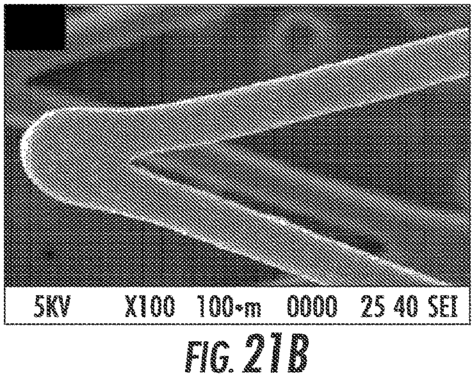
Figure 21C:
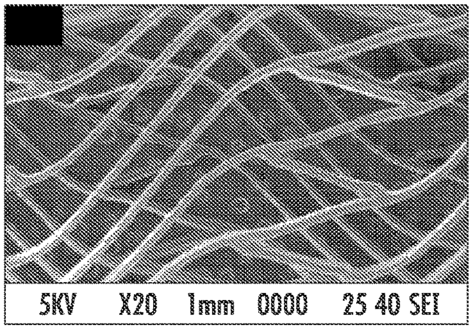
Figure 21D:
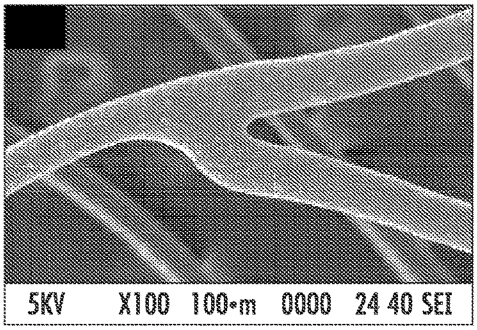

The KDR profiles of MDES053A and MDES053B post-simulated deployment using a 6 Fr catheter are depicted in FIG. 20. For comparison, the KDR profile of a stent with the same coating features post simulated deployment using a 7.5 Fr catheter is also plotted in FIG. 20. These three stents have comparable KDR profiles, except the stents crimped into the 6 Fr catheter exhibit more initial burst release. Overall, MDES053A and MDES053B are compatible with a 6 Fr catheter system.

Example 10

S.M.A.R.T.® Vascular and S.M.A.R.T.® Flex Platform

The PLCL/PLA (25:75)-based formulations were coated onto the S.M.A.R.T.® Vascular and S.M.A.R.T.® Flex bare metal stents, which exhibit drastically different stent designs, see Table 9. The DC/TC coating formulations result in conformal coatings on both stents. After simulated deployment using a 7.5 Fr catheter, the coatings remain intact in both cases (FIG. 21) as seen for other BMS platforms.

TABLE 9

Coated S.M.A.R.T. Vascular and S.M.A.R.T. Flex stents

| Group | Stent | PTx in DC (wt %) | DC polymer composition | DC mass (mg/10 mm) | TC polymer composition | TC mass (mg/10 mm) | PTx loading (μg/10 mm) |
|---|---|---|---|---|---|---|---|
| MDES056B | S.M.A.R.T. Vascular | 35 | PLCL/PLA (25:75) | 1.0 | PLCL/PLA (25:75) | 2.0 | 35 |
| MDES056C | S.M.A.R.T. Flex | | | | | | |

Note:
mg/10 mm refer to mg of material per 10 mm of stent length

Figure 22:
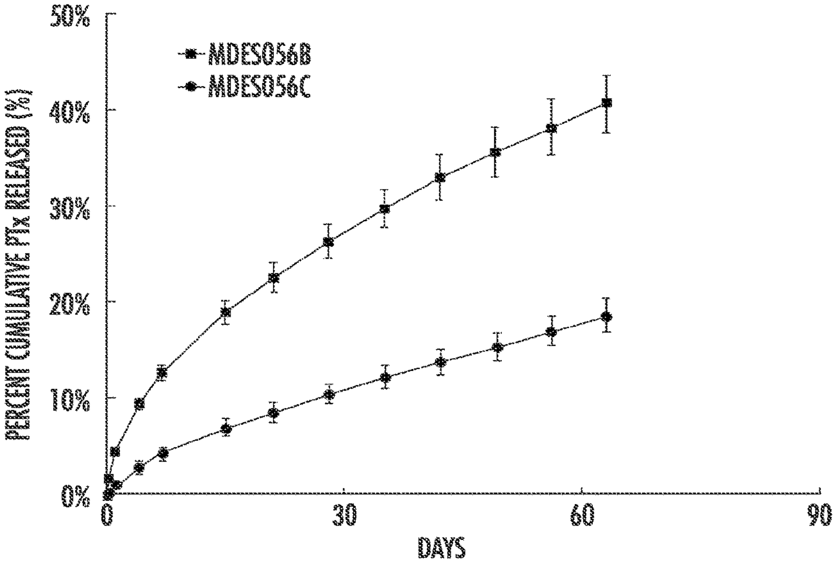
FIG. 22 is a graph showing cumulative percent mass of PTx released from coated S.M.A.R.T.® Vascular (MDES056B) and S.M.A.R.T.® Flex (MDES056C) stents as a function of time.

Stents MDES056B and MDES056C were subject to KDR evaluation post simulated deployment using a 7.5 Fr catheter. FIG. 22 shows the corresponding drug release profiles.

Example 11

Supera® Platform

Figure 23A:
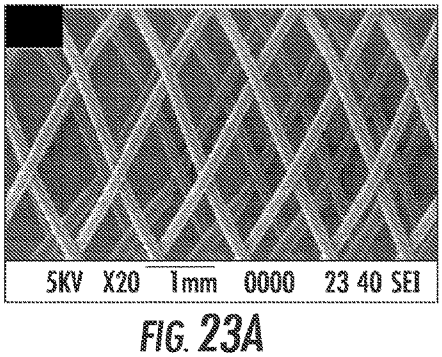
FIG. 23A and FIG. 23B are (FIG. 23A) low and (FIG. 23B) high magnification SEM images of MDES056A (6.5 mm Supera®) post simulated deployment using a 7.5 Fr catheter.
Figure 23B:
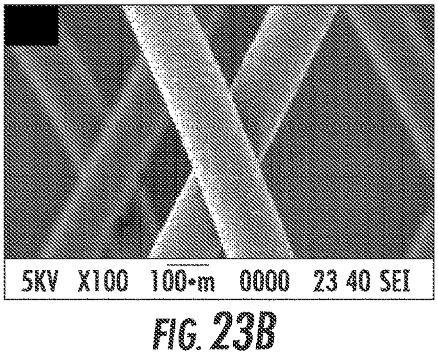

The Supera® stent comprises six-pairs of closed-ended interwoven nitinol wires that are arranged in a helical pattern designed to be both flexible and resistant to fracture. During crimping, the nitinol wires slide over each other. Consequently, coating drug/polymer onto such stents is challenging, as the coatings may potentially be torn when a coated Supera® stent is loaded into a catheter. When the PLCL/PLA (25:75)-based formulations were coated onto the Supera® stent, a conformal coating over the nitinol wires was obtained. As shown in FIG. 23, the coating was intact post simulated deployment using a 7.5 Fr catheter.

Figure 24:
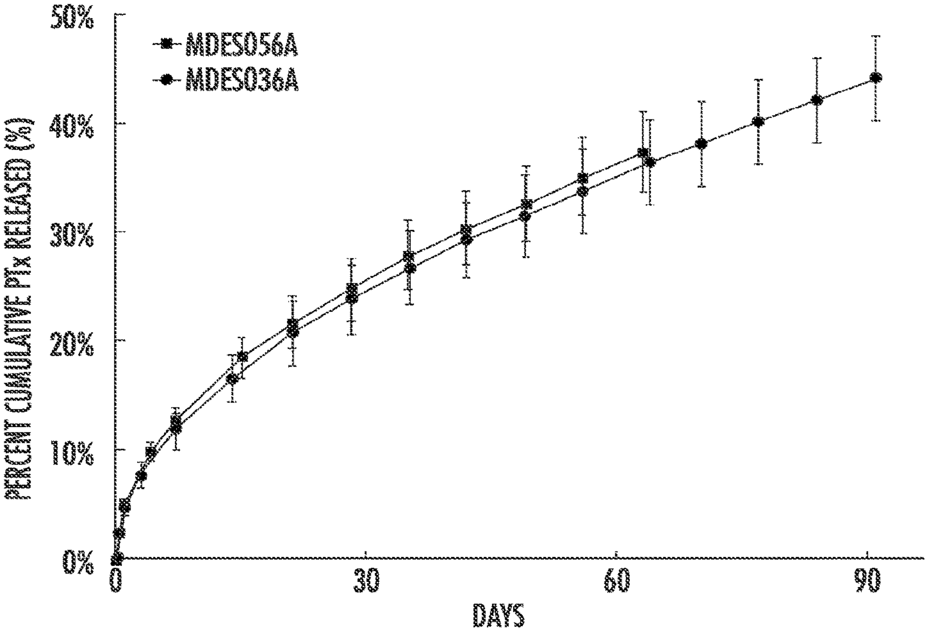
FIG. 24 is a graph showing KDR profile of PTx coated Supera® stent MDES056A with MDES036A as reference.

FIG. 24 depicts the KDR profile of the coated Supera® stent MDES056A post simulated deployment using a 7.5 Fr catheter. The Supera stent is a braid with round strut cross-sections, while the LifeStent® stent is laser-cut and its struts have rectangular cross-sections. However, these two types of MDES show essentially the same KDR profile when coated with the same DC/TC coatings.

What is claimed:

1. A coated stent comprising (a) a tubular metallic substrate, (b) a first coating at least partially covering said substrate, said first coating comprising a first biodegradable polymer or blend of biodegradable polymers, and paclitaxel, wherein the total amount of paclitaxel in the stent is in the range of from 10 ug/10 mm length of stent to 80 ug/10 mm length of stent, and (c) a second coating at least partially covering said first coating, said second coating comprising a second biodegradable polymer or blend of biodegradable polymers, said second coating not containing a therapeutic agent, wherein said first biodegradable polymer or blend of biodegradable polymers is the same or different from the second biodegradable polymer or blend of biodegradable polymers; and wherein the first coating thickness is from 1 to 15 microns and the second coating thickness is from 1 to 35 microns.

2. The coated stent of claim 1, wherein the first coating is configured to release a quantity of paclitaxel equal to 12.5 ng/$mm^2$ of stent surface area per day or less, during a period of from one to four days of submersion in a pH 7.4 phosphate-buffered saline buffer solution containing 2 wt % sodium dodecyl sulfate at 37° C. under action of a rotary shaker, when the buffer solution is removed completely weekly for paclitaxel quantification and replaced with fresh buffer solution.

3. A coated stent comprising (a) a tubular metallic substrate, (b) a first coating at least partially covering said substrate, said coating comprising a blend of poly(L-lactide-co-c-caprolactone) (PLCL), poly(L-lactide) (PLA), and paclitaxel and (c) a second coating at least partially covering said first coating, said second coating comprising PLCL and PLA, wherein the first coating comprises 10 to 99 wt percent of PLCL, 1 to 90 wt percent of PLA and paclitaxel and wherein said second coating does not contain a therapeutic agent, wherein the total amount of paclitaxel in the stent is in the range of from 10 ug/10 mm length of stent to 80 ug/10 mm length of stent.

4. The coated stent of claim 3, wherein the first coating is configured to release paclitaxel such that the quantity of paclitaxel released, based on a total amount of paclitaxel in the coated stent, ranges from 2% to 4% each week from 6 weeks to 20 weeks of submersion in a pH 7.4 phosphate-buffered saline buffer solution containing 2 wt % sodium dodecyl sulfate at 37° C. under action of a rotary shaker, when the buffer solution is removed weekly for paclitaxel quantification and replaced with fresh buffer solution.

5. The coated stent of claim 3, wherein said tubular body comprises at least one strand, the at least one strand forming a plurality of intersections at which portions of the at least one strand overlap with each other.

6. The coated stent of claim 5, wherein the helical metallic strands comprise nitinol.

7. The coated stent of claim 3, wherein the PLCL has a molar percentage of lactide ranging from 60% to 80% and a molar percentage of caprolactone ranging from 20% to 40%.

8. The coated stent of claim 3, wherein the weight ratio of PLCL to PLA in each of the first coating and the second coating ranges from 15:85 to 35:65.

9. The coated stent of claim 3, wherein the weight ratio of PLCL to PLA in each of the first coating and the second coating ranges from 40:60 to 60:40.

10. The coated stent of claim 3, wherein the weight ratio of PLCL to PLA in each of the first coating and the second coating ranges from 45:55 to 55:45.

* * * * *